(12) United States Patent
Fisher et al.

(10) Patent No.: US 8,003,769 B2
(45) Date of Patent: *Aug. 23, 2011

(54) DYE-LABELED RIBONUCLEOTIDE TRIPHOSPHATES

(75) Inventors: Peter Virgil Fisher, El Granada, CA (US); Shaheer Khan, Foster City, CA (US); Paolo Vatta, San Mateo, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/656,305

(22) Filed: Jan. 25, 2010

(65) Prior Publication Data

US 2010/0292457 A1    Nov. 18, 2010

Related U.S. Application Data

(60) Continuation of application No. 11/797,586, filed on May 4, 2007, now Pat. No. 7,678,892, which is a division of application No. 11/006,691, filed on Dec. 8, 2004, now Pat. No. 7,262,029, which is a division of application No. 09/886,011, filed on Jun. 22, 2001, now Pat. No. 6,887,690.

(51) Int. Cl.
*C07G 3/00* (2006.01)
*C07H 21/02* (2006.01)
*C12Q 1/68* (2006.01)

(52) U.S. Cl. .............. 536/4.1; 536/23.1; 435/6
(58) Field of Classification Search .............. 536/4.1, 536/23.1; 435/6
See application file for complete search history.

(56) References Cited

U.S. PATENT DOCUMENTS

| | | | |
|---|---|---|---|
| 4,656,171 A | 4/1987 | Austel et al. |
| 4,670,438 A | 6/1987 | Austel et al. |
| 4,722,929 A | 2/1988 | Austel et al. |
| 4,746,658 A | 5/1988 | Austel et al. |
| 5,177,074 A | 1/1993 | Allen et al. |
| 5,188,934 A | 2/1993 | Menchen et al. |
| 5,366,860 A | 11/1994 | Bergot et al. |
| 5,652,099 A | 7/1997 | Conrad |
| 5,654,442 A | 8/1997 | Menchen et al. |
| 5,728,525 A | 3/1998 | Conrad |
| 5,728,529 A | 3/1998 | Metzker et al. |
| 5,763,167 A | 6/1998 | Conrad |
| 5,800,996 A | 9/1998 | Lee et al. |
| 5,840,999 A | 11/1998 | Benson et al. |
| 5,847,162 A | 12/1998 | Lee et al. |
| 5,863,727 A | 1/1999 | Lee et al. |
| 5,885,778 A | 3/1999 | Menchen et al. |
| RE36,187 E | 4/1999 | Townsend et al. |
| 5,936,087 A | 8/1999 | Benson et al. |
| 5,939,292 A | 8/1999 | Gelfand et al. |
| 5,945,526 A | 8/1999 | Lee et al. |
| 6,008,379 A | 12/1999 | Benson et al. |
| 6,020,481 A | 2/2000 | Benson et al. |
| 6,025,505 A | 2/2000 | Lee et al. |
| 6,027,709 A | 2/2000 | Little et al. |
| 6,051,719 A | 4/2000 | Benson et al. |
| 6,080,852 A | 6/2000 | Lee et al. |
| 6,096,723 A | 8/2000 | Menchen et al. |
| 6,096,875 A | 8/2000 | Khan et al. |
| 6,111,116 A | 8/2000 | Benson et al. |
| 6,121,296 A | 9/2000 | Schramm et al. |
| 6,191,278 B1 | 2/2001 | Lee et al. |
| 6,194,576 B1 | 2/2001 | Nguyen-Ba et al. |
| 6,197,555 B1 | 3/2001 | Khan et al. |
| 6,197,956 B1 | 3/2001 | Randall et al. |
| 6,221,604 B1 | 4/2001 | Upadhya et al. |
| 6,221,606 B1 | 4/2001 | Benson et al. |
| 6,500,650 B1 | 12/2002 | Stanton et al. |
| 6,723,509 B2 | 4/2004 | Ach |
| 6,887,690 B2 | 5/2005 | Fisher et al. |
| 7,262,029 B2 | 8/2007 | Fisher et al. |
| 7,678,892 B2 * | 3/2010 | Fisher et al. .............. 536/4.1 |
| 2005/0250119 A1 | 11/2005 | Taing et al. |

FOREIGN PATENT DOCUMENTS

WO    WO-03/000841    1/2003

OTHER PUBLICATIONS

Rosenblum et al., Nucleic Acids Research, 1997, pp. 4500-4504, vol. 25.
US02/16587, International Search Report mailed Feb. 19, 2003.

* cited by examiner

*Primary Examiner* — Jezia Riley

(57) ABSTRACT

The invention provides novel dye-labeled ribonucleotide analogs and methods for synthesizing those analogs. The compounds of the invention are especially useful for DNA sequencing by the polymerase chain reaction.

12 Claims, 4 Drawing Sheets
(4 of 4 Drawing Sheet(s) Filed in Color)

DYE-LABELED RIBONUCLEOTIDE TRIPHOSPHATES

The U.S. Government has a paid-up license in this invention and the right in limited circumstances to require the patent owner to license others on reasonable terms as provided for by the terms of Award No. 70NANB8H4002 awarded by the National Institute of Standards and Technology (NIST) to the Perkin-Elmer Corp., Applied Biosystems Division.

This application is a continuation of application Ser. No. 11/797,586, filed May 4, 2007, now allowed, which is a division of application Ser. No. 11/006,691, filed Dec. 8, 2004, now U.S. Pat. No. 7,262,029, which is a division of application Ser. No. 09/886,011, filed Jun. 22, 2001, now U.S. Pat. No. 6,887,690, all of which are incorporated by reference herein.

INTRODUCTION

The development of reliable methods for determining the sequence of DNA (deoxyribonucleic acid) and RNA (ribonucleic acid) has been essential to the success of recombinant DNA and genetic engineering. When used with the other techniques of modern molecular biology, nucleic acid sequencing allows the dissection of animal, plant, and viral genomes into discrete genes with defined chemical structures. Once a gene has been isolated and characterized, it can be modified to produce desired changes in its sequence that allow the production of a gene product with properties different from those of the original gene product.

The development of nucleic acid sequencing methods has involved parallel advances in a variety of techniques. One was the emergence of simple and reliable methods for cloning small to medium-sized strands of DNA into bacterial plasmids, bacteriophages, and animal viruses. Cloning allowed the production of pure DNA in sufficient quantities to allow chemical analysis. Another was the use of gel electrophoretic methods for the high resolution separation of oligonucleotides on the basis of size. The key development, however, was the introduction of methods of generating sets of fragments of cloned, purified DNA that contain, in their collection of lengths, the information necessary to define the sequence of the nucleotides comprising the parent DNA molecules.

Presently, there are several approaches to determining the sequence of a DNA template, see, e.g., the dideoxy chain termination method, Sanger et al., Proc. Natl. Acad. Sci., 74:5463-67 (1977); the chemical degradation method, Maxam et al., Proc. Natl. Acad. Sci., 74:560-564 (1977); and hybridization methods, Drmanac et al., Genomics, 4:114-28 (1989), Khrapko, FEB 256:118-22 (1989). The most commonly used methods for DNA sequencing are based on the dideoxy chain termination method of Sanger et al., which involves enzymatic synthesis of single strands of DNA from a single stranded DNA template and a primer.

The basic dideoxy sequencing procedure involves (i) annealing an oligonucleotide primer to a template; (ii) extending the primer with DNA polymerase in four separate reactions, each containing a labeled nucleotide or a labeled primer, a mixture of unlabeled dNTPs, and one chain-terminating ddNTP; (iii) resolving the four sets of reaction products by means of, for example, high-resolution denaturing polyacrylamide/urea gel electrophoresis, capillary separation, or other resolving means; and (iv) producing an autoradiographic image of the gel that can be examined to infer the sequence. Alternatively, if a dye-labeled primer or dideoxynucleotide is used, for example, in automated sequencing procedures using Applied Biosystems Prism® 310, 3100, 3700, or 377, the chain-terminated fragments can be resolved and detected by fluorometry.

In the basic dideoxy chain termination method, four separate syntheses are carried out. In each, a single-stranded template is provided along with a primer, for example, a synthetic oligonucleotide or a restriction fragment, that hybridizes to the template. In each of the four sequencing reactions, the primer is elongated at its 3'-terminus using a DNA polymerase in the presence of enough of a chain terminating analog of one of the four possible deoxynucleotides, for example, a dideoxynucleotide (ddNTP), so that the growing chains are randomly terminated by the 3'-incorporation of these "deadend" nucleotides. The concentration of chain terminating nucleotide relative to that of deoxynucleotides is adjusted to give a spread of termination events corresponding to all the possible chain lengths that can be resolved by gel electrophoresis. Enzymes currently used for this method of sequencing include: the large fragment of *Escherichia coli* DNA polymerase I ("Klenow" fragment), reverse transcriptase, *Thermus aquaticus* (Taq) DNA polymerase, and a modified form of bacteriophage T7 DNA polymerase (e.g., Sequenase®).

The four DNA synthesis reactions produce four sets of DNA products, each product having one defined terminus and one variable terminus. The defined terminus starts with the primer molecule. The variable terminus ends with a chain terminating agent specific for the nucleotide base (either G, A, T, or C) at which the synthesis reaction terminated. The four sets of products are each separated on the basis of their molecular weight, in four separate lanes of a high resolution polyacrylamide gel, to form four series of bands, with each band on the gel corresponding sequentially to a specific nucleotide in the DNA sequence. Thus, the relative positions of the bands identify the positions in the DNA sequence of each given nucleotide base. Generally, the DNA products are labeled, for example, by including a radioactive nucleotide (e.g., $^{35}$S-dATP, $^{32}$P-dATP) in each reaction, so that the bands produced are readily detected. Because the products from each of the four synthesis reactions must be run in separate gel lanes, problems frequently arise when comparing band mobilities between the different lanes.

The chain termination method has been modified in several ways, and serves as the basis for all currently available automated DNA sequencing methods. See, e.g., Sanger et al., J. Mol. Biol., 143:161-78 (1980); Schreier et al., J. Mol. Biol., 129:169-72 (1979); Smith et al., Nucleic Acids Research, 13:2399-2412 (1985); Smith et al., Nature, 321:674-79 (1987), U.S. Pat. No. 5,171,534; Prober et al., Science, 238: 336-41 (1987); Section II, Meth. Enzymol., 155:51-334 (1987); Church et al., Science, 240:185-88 (1988); Swerdlow et al., Nucleic Acids Research, 18: 1415-19 (1989); Ruiz-Martinez et al., Anal. Chem., 2851-58 (1993); Studier, PNAS, 86:6917-21 (1989); Kieleczawa et al., Science, 258:1787-91; and Connell et al., Biotechniques, 5:342-348 (1987).

Two modifications of the original dideoxy method, which are commonly used for automated DNA sequencing, are referred to as dye-primer sequencing and dye-terminator sequencing. In dye-primer sequencing, a fluorescently-labeled primer is used in combination with unlabeled ddNTPs. The procedure requires four synthesis reactions and up to four lanes on a gel for each template sequenced (i.e., one lane for each of the base-specific termination products). Following extension of the fluorescently-labeled primer, the sequencing reaction mixtures containing ddNTP termination products are separated by electrophoresis on a DNA sequencing gel.

The size-separated, fluorescently-labeled products are automatically scanned with a laser at the bottom of the gel and the fluorescence is detected with an appropriate monitor. (Smith et al., 1986, Nature 321:674-679, which is incorporated herein by reference). In a modification of this method, the primer added to each of the four reactions is labeled with a different fluorescent marker. After the four separate sequencing reactions are completed, the reactions are combined and the mixture is subjected to gel analysis in a single lane. The different fluorescent labels (one corresponding to each of the four different base-specific termination products) are individually detected.

Alternatively, in dye-terminator sequencing, a DNA polymerase is used to incorporate dNTPs onto the growing end of an unlabeled DNA primer until the enzyme incorporates a chain-terminating, fluorescently-labeled ddNTP (Lee et al., 1992, Nucleic Acid Research 20:2471). This process offers the advantage of not having to synthesize dye-labeled primers. If each different ddNTP is labeled with a different fluorescent marker, all four reactions can be performed in the same tube.

The availability of thermoresistant polymerases, such as Taq polymerase, has led to improved methods for sequencing, referred to as "cycle sequencing," many of which are compatible with automated sequencing protocols. See U.S. Pat. No. 5,075,216, which is incorporated herein by reference. In cycle sequencing, cycles of heating and cooling are repeated allowing numerous extension products to be generated from each molecule of target. Murray, 1989, Nucleic Acids Research 17:8889, which is incorporated herein by reference. The amplification of target sequences complementary to the template sequence, in the presence of dideoxy chain terminators, produces a family of extension products of all possible lengths.

Because amplification of the template is part of the procedure, cycle sequencing, in theory, permits nucleotide sequence analysis to be performed starting with small quantities of DNA. In practice, however, template quantity is often a limiting factor in cycle sequencing because (1) the amplification of chain-terminated templates is linear, not exponential as for full-length templates and (2) Taq DNA polymerase discriminates against the incorporation of unconventional nucleotides, such as ddNTPs.

To achieve adequate incorporation of ddNTPs, DNA sequencing with thermostable DNA polymerases is performed using a mixture in which the chain-terminating nucleotide is present at a high concentration relative to the concentration of the dNTPs, thus ensuring that a population of extension products representing all possible fragment lengths over a distance of several hundred bases will be generated. Because ddNTPs are expensive, cycle sequencing protocols achieve the desired ddNTP:dNTP concentration ratio by using very low concentrations of the conventional dNTPs. Such reaction mixtures create an environment wherein the thermostable polymerase is essentially starved for nucleotide substrates and DNA amplification is therefore very inefficient. Consequently, when the amount of template is below 10 ng per 100 bp, the cycle sequencing reaction is either very weak or fails completely.

Modified thermostable DNA polymerases having reduced discrimination against ddNTPs have been described. See European Patent No. 0 655 506 A1; U.S. Pat. No. 5,614,365. One example of a modified thermostable DNA polymerase is the mutated form of *T. aquaticus* DNA polymerase having a tyrosine residue at position 667 (instead of a phenylalanine residue), i.e. the F667Y mutated form of Taq DNA polymerase. AmpliTaq® FS, manufactured by Roche Diagnostics Corp. (Indianapolis, Ind.) and marketed through Applied Biosystems, Inc. (Foster City, Calif.), reduces the amount of ddNTP required for efficient nucleic acid sequencing of a target by hundreds to thousands-fold. AmpliTaq® FS is a mutated form of *T. aquaticus* DNA polymerase having the F667Y mutation and additionally an aspartic acid residue at position 46 (instead of a glycine residue; G46D mutation). Cycle sequencing methods using such mutant DNA polymerases, however, still use chain terminators and, thus, do not offer the user the option of amplifying the reaction products in a geometric manner. When used to sequence small amounts of DNA starting material, these methods, therefore, often require a first PCR amplification reaction and, then, a second cycle sequencing reaction.

Certain modified thermostable DNA polymerases have reduced discrimination against ribonucleotides. See U.S. Pat. No. 5,939,292, which is incorporated herein by reference. When these enzymes are used in PCR methods, concentrations of dNTPs and/or rNTPs that are optimal for target amplification may be employed. Unlike ddNTPs, incorporation of an rNTP does not result in a chain termination event, and, therefore, amplification in the presence of rNTPs is geometric.

SUMMARY OF THE INVENTION

The present invention provides dye-labeled ribonucleotides, which are useful substrates for direct PCR sequencing (DPCRS) and other methods involving the synthesis of labeled polynucleotides, which will be apparent to those of skill in the art. The dye-labeled ribonucleotide analogs of the invention are efficiently incorporated into primer extension products by modified thermostable DNA polymerases. The compounds of the invention are useful in DNA sequencing, in detecting polymorphisms, and in generating dye-labeled polynucleotides.

It is accordingly an object of the invention to provide methods for preparing dye-labeled ribonucleotide analogs. It is a further object of the invention to provide methods for using dye-labeled ribonucleotide analogs in improved methods for DNA sequence analysis and for the preparation of dye-labeled DNAs and RNAs, which may be used, for example, as hybridization probes.

In one embodiment, the invention provides ribonucleotide analogs coupled to dyes through propargyl-ethyl-oxide-amino (EO) or propargylamino (PA) linkers.

In another embodiment, the invention provides dye-labeled purine analogs having linkers that form intramolecular hydrogen bonds or chelates, thereby increasing the rigidity of the nucleotide analog and decreasing the steric interactions between substituents linked at the C8 position of a purine or the C7 position of a 7-deazapurine and 5'-O-phosphorylated sugars. For purines, linkers at the C8 position form intramolecular hydrogen bonds or chelates with the corresponding nitrogen atom at position 7. For 7-deazapurines, linkers at C7 form intramolecular hydrogen bonds or chelates with the corresponding functional group at position 6.

In another embodiment, the invention provides dye-labeled pyrimidine analogs having linkers at the C5 position that form intramolecular hydrogen bonds or chelates with the corresponding atom or atoms at position 6, thereby altering the spatial orientation of the linker to, for example, enhance incorporation efficiency by a DNA polymerase.

In another embodiment, the invention provides dye-labeled purine analogs having linkers at the C8 position that are covalently linked to the 5' carbon of the sugar, thereby locking the nucleoside in a conformation that may favor incorporation by an polymerase enzyme.

In another embodiment, the invention provides dye-labeled pyrimidine analogs having substituents at the C4 position that are covalently linked to the 5' carbon of the sugar, thereby locking the nucleoside in a conformation that may favor incorporation by an polymerase enzyme.

In another embodiment, the invention provides dye-labeled ribonucleotide analogs having tuned linkers that may reduce or eliminate mobility differences between polynucleotides comprising different analogs, for example, during polyacrylamide gel electrophoresis.

In another embodiment, the invention provides sets of dye-labeled ribonucleotide analogs matched for peak height evenness and relative mobility during polyacrylamide gel electrophoresis.

In another embodiment, the invention provides a method for determining the sequence of a DNA template in a single reaction using sets of dye-labeled ribonucleotide analogs.

In another embodiment, the invention provides a method for detecting single nucleotide polymorphisms (SNPs) using dye-labeled ribonucleotide analogs.

In another embodiment, the invention provides a method for preparing randomly-fragmented dye-labeled hybridization probes.

In another embodiment, the invention provides a method for preparing dye-labeled sense and antisense RNAs.

Additional objects and advantages of the invention will be set forth in part in the description which follows, and in part will be apparent from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and do not limit or restrict the invention, as claimed.

The accompanying drawings, which are incorporated in and constitute a part of this specification, illustrate several embodiments of the invention and together with the description, serve to explain the principles of the invention.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

DESCRIPTION OF THE EMBODIMENTS

Figure 1:
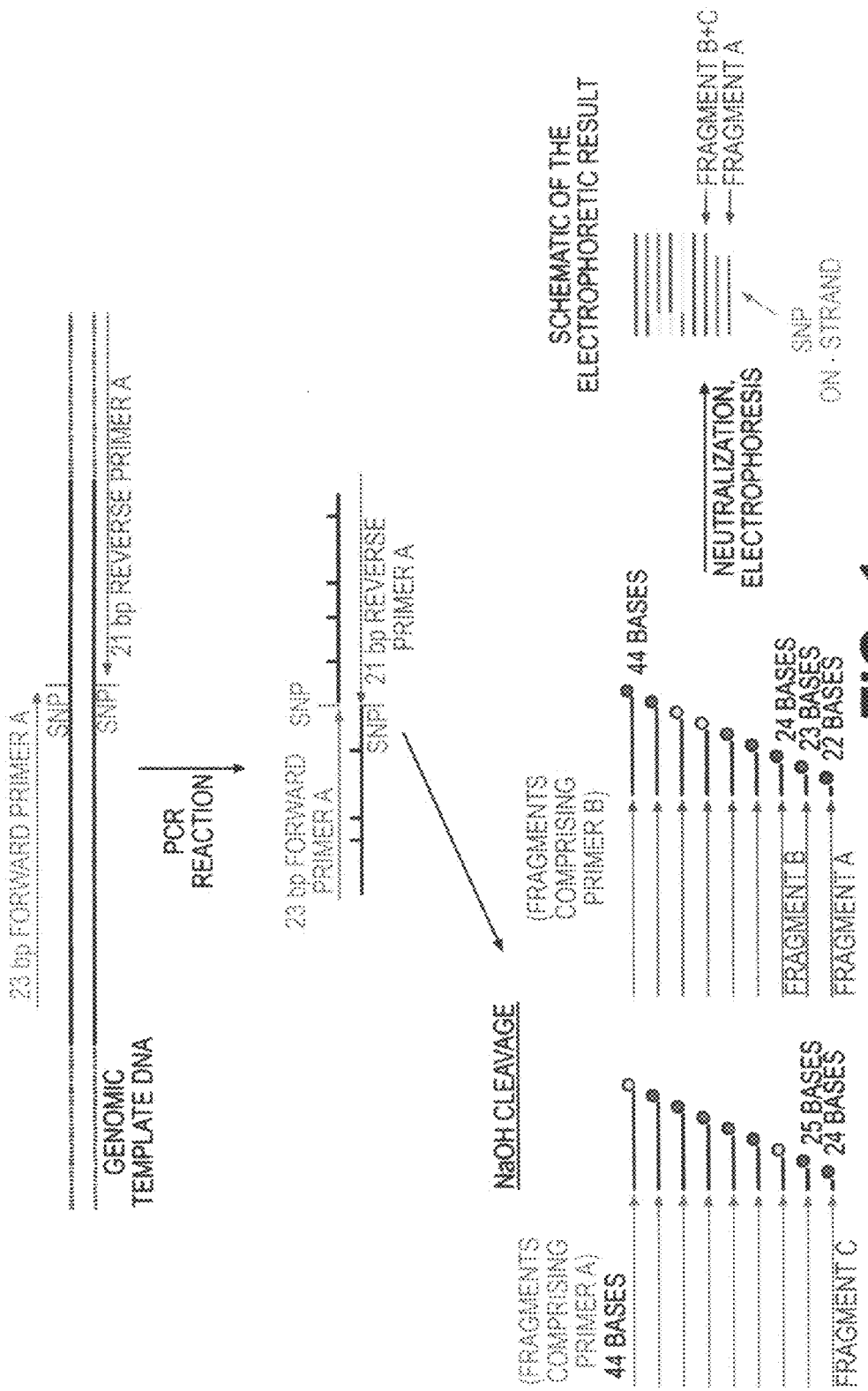
FIG. 1 shows a method for detecting a single nucleotide polymorphism (SNP) using a mixture of dye-labeled rNTPs and dNTPs.

The present invention provides novel compositions that are dye-labeled ribonucleotide analogs, which may be incorporated in polynucleotides. Methods for using the ribonucleotide analogs of the invention for DNA sequencing, for detecting mutations, and for preparing dye-labeled polynucleotides also are provided. The nucleotide analogs of the invention enable the practice of novel methods for these purposes, which are advantageous over prior procedures.

To facilitate the understanding of the invention, a number of terms are defined below.

The term "nucleobase" means a nitrogen-containing heterocyclic moiety capable of forming Watson-Crick hydrogen bonds in pairing with a complementary nucleobase or nucleobase analog, e.g., a purine, a 7-deazapurine, or a pyrimidine. Typical nucleobases are the naturally occurring nucleobases adenine, guanine, cytosine, uracil, thymine, and analogs of the naturally occurring nucleobases, e.g., 7-deazaadenine, 7-deazaguanine, 7-deaza-8-azaguanine, 7-deaza-8-azaadenine, inosine, nebularine, nitropyrrole, nitroindole, 2-amino-purine, 2,6-diamino-purine, hypoxanthine, pseudouridine, pseudocytidine, pseudoisocytidine, 5-propynyl-cytidine, isocytidine, isoguanine, 7-deaza-guanine, 2-thio-pyrimidine, 6-thio-guanine, 4-thio-thymine, 4-thio-uracil, $O^6$-methyl-guanine, $N^6$-methyl-adenine, $O^4$-methyl-thymine, 5,6-dihydrothymine, 5,6-dihydrouracil, 4-methyl-indole, and ethenoadenine (Fasman, *Practical Handbook of Biochemistry and Molecular Biology*, pp. 385-394, CRC Press, Boca Raton, Fla., 1989).

As used herein, "nucleoside" refers to a compound consisting of a nucleobase linked to the C-1' carbon of a ribose sugar. The ribose may be substituted or unsubstituted. Substituted ribose sugars include, but are not limited to, those riboses in which one or more of the carbon atoms, for example the 2'-carbon atom, is substituted with one or more of the same or different Cl, F, —R, —OR, —NR$_2$, or halogen groups, where each R is independently H, $C_1$-$C_6$ alkyl, or $C_5$-$C_{14}$ aryl. Ribose examples include ribose, 2'-deoxyribose, 2',3'-dideoxyribose, 2'-haloribose, 2'-fluororibose, 2'-chloribose, and 2'-alkylribose, e.g., 2'-O-methyl, 4'-α-anomeric nucleotides, 1'-α-anomeric nucleotides, 2'-4'- and 3'-4'-linked and other "locked" or "LNA", bicyclic sugar modifications (WO 98/22489; WO 98/39352; WO 99/14226). LNA sugar analogs within an oligonucleotide are represented by the structures:

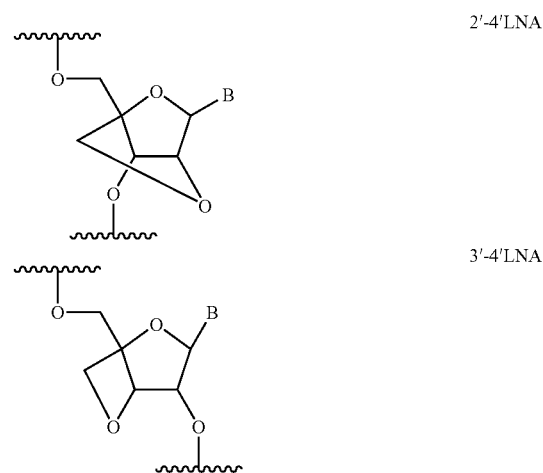

where B is any nucleobase.

Modifications at the 2'- or 3'-position of ribose include hydrogen, hydroxy, methoxy, ethoxy, allyloxy, isopropoxy, butoxy, isobutoxy, methoxyethyl, alkoxy, phenoxy, azido, amino, alkylamino, fluoro, chloro, and bromo. When the nucleobase is purine, e.g., A or G, the ribose sugar is attached to the $N^9$-position of the nucleobase. When the nucleobase is pyrimidine, e.g., C, T or U, the pentose sugar is attached to the $N^1$-position of the nucleobase (Kornberg and Baker, *DNA Replication*, $2^{nd}$ Ed., Freeman, San Francisco, Calif., 1992).

The term "nucleotide" refers to a phosphate ester of a nucleoside, as a monomer unit or within a nucleic acid. Nucleotides are sometimes denoted as "rNTP", "NTP", "dNTP" and "ddNTP" to particularly point out the structural features of the ribose sugar, as illustrated by the structures:

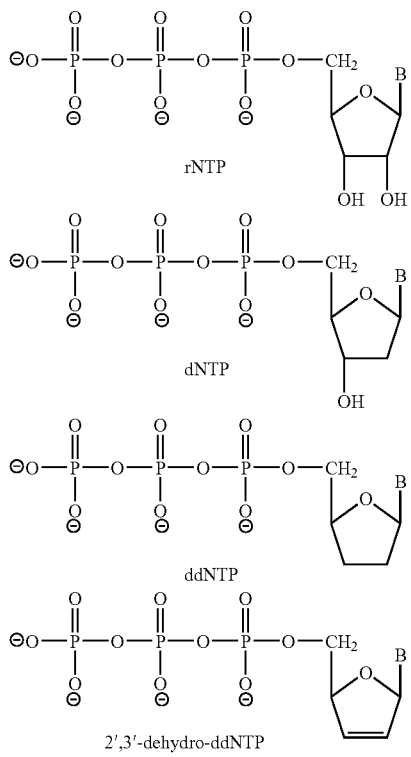

where B is a nucleobase. "Ribonucleotide 5'-triphosphate" refers to rNTP, a ribonucleotide with a triphosphate ester group at the 5' position. The triphosphate ester group may include sulfur substitutions for the various oxygens, e.g., α-thio-nucleotide 5'-triphosphates. Nucleosides and nucleotides include the natural D optical isomer, as well as the L optical isomer forms (Garbesi (1993) Nucl. Acids Res. 21:4159-65; Fujimori (1990) J. Amer. Chem. Soc. 112:7435; Urata, (1993) Nucleic Acids Symposium Ser. No. 29:69-70).

The terms "polynucleotide" or "oligonucleotide" are used herein interchangeably and mean single-stranded and double-stranded polymers of nucleotide monomers, including 2'-deoxyribonucleotides (DNA) and ribonucleotides (RNA) linked by internucleotide phosphodiester bond linkages, or internucleotide analogs, and associated counter ions, e.g., $H^+$, $NH_4^+$, trialkylammonium, $Mg^{2+}$, $Na^+$, and the like. A polynucleotide may be composed entirely of deoxyribonucleotides, entirely of ribonucleotides, or chimeric mixtures thereof. Polynucleotides may be comprised of nucleobase and sugar analogs. Polynucleotides typically range in size from a few monomeric units, e.g., 5-40, when they are frequently referred to in the art as oligonucleotides, to several thousands of monomeric nucleotide units. Unless denoted otherwise, whenever a polynucleotide sequence is represented, it will be understood that the nucleotides are in 5' to 3' order from left to right and that "A" denotes deoxyadenosine, "C" denotes deoxycytidine, "G" denotes deoxyguanosine, and "T" denotes thymidine.

The term "primer" as used herein refers to an oligonucleotide, whether natural or synthetic, that is capable of acting as a point of initiation of nucleic acid synthesis under conditions in which primer extension is initiated. The appropriate length of a primer depends on the intended use of the primer, but typically ranges from 15 to 35 nucleotides. Short primer molecules generally require cooler temperatures to form sufficiently stable hybrid complexes with the template. A primer need not reflect the exact sequence of the template but must be sufficiently complementary to hybridize with a template for primer elongation to occur.

Primers and nucleotides of the present invention may be labeled with moieties that affect the rate of electrophoretic migration, i.e. mobility-modifying labels. Mobility-modifying labels include, but are not limited to biotin, fluorescent dyes, cholesterol, and polyethyleneoxy units, $-(CH_2CH_2O)_n-$, where n may be 1 to 100 (Grossman et al., U.S. Pat. No. 5,624,800). Preferably, n is from 2 to 20. The polyethyleneoxy (PEO) units may be interspersed with charged groups, such as phosphodiester to impart charge and increase electrophoretic mobility (velocity). The PEO label may be uncharged and act to retard electrophoretic or chromatographic mobility. Such modifiers may serve to influence or normalize the electrophoretic velocity of amplification products during analysis, e.g., by fluorescent detection, to improve resolution and separation (Grossman et al., U.S. Pat. No. 5,470,705).

Nucleotides labeled with a reporter dye and a mobility-modifier allow for separation by electrophoresis of the primer extension fragments from fragments without mobility-modifiers, substantially independent of the size, i.e., number of nucleotides. That is, polynucleotides of the same length may be discriminated by detection of spectrally resolvable dye labels and separated on the basis of mobility-modifying labels.

Primers labeled with a mobility-modifier and used in primer extension with the reporter-labeled ribonucleotides of the invention generate fragments that may be separated from fragments generated from primers that are not labeled. In this manner, opposing strands of a double-stranded target nucleic acid may be sequenced.

Another class of labels serve to effect the separation or immobilization of labeled fragments by specific or non-specific capture means, e.g., biotin; 2,4-dinitrophenyl (DNP); and digoxigenin (Andrus, A. "Chemical methods for 5' non-isotopic labelling of PCR probes and primers" (1995) in PCR 2: A Practical Approach, Oxford University Press, Oxford, pp. 39-54).

As used herein, "alkyl" means a saturated or unsaturated, branched, straight-chain, branched, or cyclic hydrocarbon radical derived by the removal of one hydrogen atom from a single carbon atom of a parent alkane, alkene, or alkyne. Typical alkyl groups consist of 1 to 12 saturated and/or unsaturated carbons, including, but not limited to, methyl, ethyl, propyl, butyl, and the like.

As used herein, "alkyldiyl" means a saturated or unsaturated, branched, straight chain or cyclic hydrocarbon radical of 1 to 20 carbon atoms, and having two monovalent radical centers derived by the removal of two hydrogen atoms from the same or two different carbon atoms of a parent alkane, alkene or alkyne. Typical alkyldiyl radicals include, but are not limited to, 1,2-ethyldiyl, 1,3-propyldiyl, 1,4-butyldiyl, and the like.

As used herein, "aryl" means a monovalent aromatic hydrocarbon radical of 6 to 20 carbon atoms derived by the removal of one hydrogen atom from a single carbon atom of a parent aromatic ring system. Typical aryl groups include, but are not limited to, radicals derived from benzene, substituted benzene, naphthalene, anthracene, biphenyl, and the like.

As used herein, the term "dye" refers to any reporter group whose presence can be detected by its light absorbing or light emitting properties. The term "dye" encompasses fluorescent compounds. The fluorescent dyes of the invention include, but are not limited to, fluorescein-type dyes, rhodamine-type dyes, cyanine-type dyes, and Energy transfer dye pairs.

The term "fluorescein-type dye" refers to a class of xanthene dye molecules, which include the following substituted fused three-ring system:

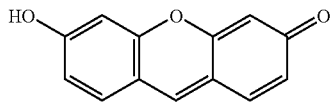

where a wide variety of substitutions are possible at each ring position. Fluorescein-type dyes are described, for example, in the following U.S. Pat. No. 5,188,943, No. 5,654,442, No. 5,840,999, No. 5,885,778, No. 6,008,379, No. 6,020,481, No. 6,096,723, and No. 6,221,604, each of which are hereby incorporated by reference herein. Examples of fluorescein-type dyes useful as fluorescent labels in DNA sequencing methods include, but are not limited to, 6-carboxyfluorescein (6-FAM), 5-carboxyfluorescein (5-FAM), 5 or 6-carboxy-4,7,2',7'-tetrachlorofluorescein (TET), 5 or 6-carboxy-4,7,2',4',5',7'-hexachlorofluorescein (HEX), 5- or 6-carboxy-4',5'-dichloro-2'7'-dimethoxyfluorescein (JOE), and 5-carboxy-2',4',5',7'-tetrachlorofluorescein (ZOE). Many times the designation −1 or −2 is placed after an abbreviation of a particular dye, e.g., HEX-1. The "−1" and "−2" designations indicate the particular 5 or 6 dye isomer being used. The 1 and 2 isomers are defined by the elution order (the 1 isomer being the first to elute) of free dye in a reverse-phase chromatographic separation system utilizing a C-8 column and an elution gradient of 15% acetonitrile/85% 0.1 M triethylammonium acetate to 35% acetonitrile/65% 0.1 M triethylammonium acetate.

The term "rhodamine-type dye" refers to a class of xanthene dye molecules which include the following fused three-ring system:

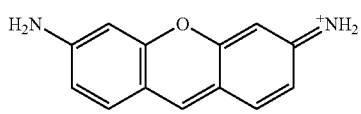

where a wide variety of substitutions are possible at each ring position. Rhodamine-type dyes are described, for example, in the following U.S. Pat. No. 5,366,860, No. 5,840,999, No. 5,847,162, No. 5,936,087, No. 6,008,379, No. 6,020,481, No. 6,025,505, No. 6,080,852, No. 6,111,116, No. 6,191,278, and No. 6,221,606, each of which is incorporated by reference herein. Exemplary rhodamine-type dyes useful as dye labels include, but are not limited to, tetramethylrhodamine (TAMRA), 4,7-dichlorotetramethyl rhodamine (dTAMRA), rhodamine X (ROX), 4,7-dichlororhodamine X (dROX), rhodamine 6G (R6G), 4,7-dichlororhodamine 6G (dR6G), rhodamine 110 (R110), 4,7-dichlororhodamine 110 (dR110), and the like (Bergot, et al., U.S. Pat. No. 5,366,860 (1994); Lee et al., Nucleic Acids Research, 20(10): 2471-2483 (1992)), with the following structures:

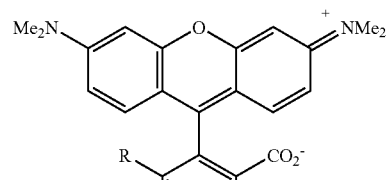

TAMRA R = H
dTAMRA R = Cl

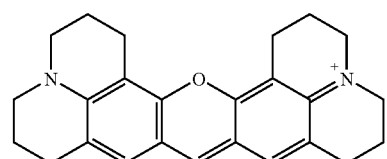

ROX R = H
dROX R = Cl

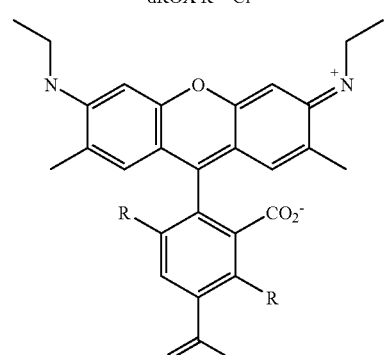

R6G R = H
dR6G R = Cl

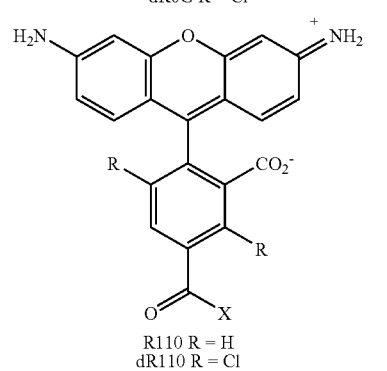

R110 R = H
dR110 R = Cl

For each of the above rhodamine-type dyes, X is the site of attachment to the linker in the compounds of the invention.

The term "cyanine-type dye" refers to a class of dye molecules with the following basic structure:

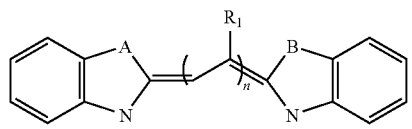

wherein A and B are independently C, O, S, or N, wherein a wide variety of substitutions are possible at each position and wherein n is generally a number from 1 to 3, but may be larger. Exemplary cyanine-type dyes useful as dye labels include, but are not limited to, the compounds disclosed in the following U.S. Pat. No. 5,986,086, No. 6,027,709, No. 6,114,350, No. 6,150,107, No. 6,197,956, No. 6,224,644, and No. 6,225,050, each of which is incorporated by reference herein.

The term "energy transfer dye pair" refers to a class of dyes in which two fluorescent dyes are covalently attached. In general, a fluorescein, or other donor dye, is attached to a rhodamine, or other acceptor dye. Energy transfer dye pairs are described, for example, in the following U.S. Pat. No. 5,800,996, No. 5,863,727, and U.S. Pat. No. 5,945,526, each of which is hereby incorporated by reference herein. An exemplary energy transfer dye pair has the structure:

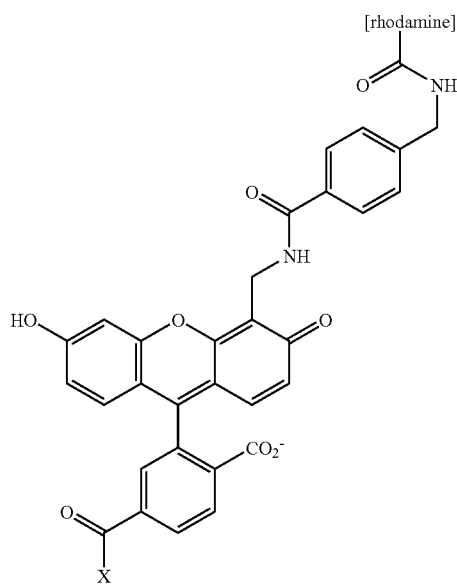

As used herein, the term "single nucleotide polymorphism" or "SNP" refers to DNA sequence variations that occur when a single nucleotide in the genome sequence is altered. SNPs occur every 100 to 300 bases along the 3-billion-base human genome in both coding (gene) and noncoding regions of the genome.

As used herein, the term "DNA sequencing reaction mixture" refers to a reaction mixture that comprises elements necessary for a DNA sequencing reaction. Thus, a DNA sequencing reaction mixture is suitable for use in a DNA sequencing method for determining the nucleic acid sequence of a target, although the reaction mixture may initially be incomplete, so that the initiation of the sequencing reaction is controlled by the user. In this manner, the reaction may be initiated once a final element, such as the enzyme, is added, to provide a complete DNA sequencing reaction mixture. Typically, a DNA sequencing reaction will contain a buffer suitable for polymerization activity, nucleoside triphosphates, and at least one unconventional nucleotide, for example a ddNTP or an rNTP. The reaction mixture also may contain a primer suitable for extension on a target by a polymerase enzyme, a polymerase, and a target nucleic acid. Either the primer or one of the nucleotides is generally labeled with a detectable moiety such as a fluorescent label. Generally, the reaction is a mixture that comprises four conventional nucleotides and at least one unconventional nucleotide. In one embodiment of the invention, the polymerase is a modified thermostable DNA polymerase and the unconventional nucleotide is a dye-labeled ribonucleotide.

The term "polymerase" refers to an enzyme that catalyzes the initiation of synthesis and the elongation of a polynucleotide chain complementary to a polynucleotide template. Polymerases may incorporate ribonucleotides, deoxyribonucleotides, modified ribonucleotides, modified deoxyribonucleotides, or combinations into the elongating chain. Polymerases may initiate polynucleotide synthesis either by recognizing specific initiation sites in the template or by extending a primer complementary to the template. Polymerases may have additional enzymatic activities including, but not limited to, 5'-3' exonuclease activity and 3'-5' exonuclease activity.

The term "thermostable polymerase" refers to an enzyme that is stable to heat, is heat resistant, and retains sufficient activity to effect subsequent primer extension reactions when subjected to the elevated temperatures for the time necessary to effect denaturation of double-stranded nucleic acids. Heating conditions necessary for nucleic acid denaturation are well known in the art and are exemplified in U.S. Pat. Nos. 4,683,202 and 4,683,195, which are incorporated herein by reference. As used herein, a thermostable polymerase is suitable for use in a temperature cycling reaction such as the polymerase chain reaction ("PCR"). For a thermostable polymerase, enzymatic activity refers to the catalysis of the combination of the nucleotides in the proper manner to form primer extension products that are complementary to a template nucleic acid strand.

The term "modified thermostable polymerase" refers to a thermostable polymerase that has been altered, for example, chemically or using recombinant DNA techniques, so that it exhibits increased efficiency in the incorporation of unconventional nucleotides.

The term "unconventional" when referring to a nucleobase, a nucleoside, or a nucleotide, includes any modification, derivations, or analogues of conventional bases, or nucleotides that naturally occur in DNA, i.e., dATP, dGTP, dCTP, and dTTP. For example, although for RNA the naturally occurring nucleotides are ribonucleotides (i.e., rATP, rGTP, rCTP, rUTP collectively rNTPs), because these nucleotides have a hydroxyl group at the 2' position of the sugar, which, by comparison is absent in dNTPs, as used herein, ribonucleotides or analogues of ribonucleotides are unconventional nucleotides for incorporation in DNA. Similarly, dideoxynucleotides also are unconventional bases. Unconventional nucleotides may be labeled with dyes, for example, fluorescein, rhodamine; dichlororhodamine (d-rhodamine), or cyanine dyes dyes.

As used herein, the term "linker" refers to moieties that form a linkage between the base portion of a ribonucleotide and a dye. Linkers useful for preparing the dye-labeled ribonucleotides of the invention include, but are not limited to moieties of the general formula:

$$-\text{(C≡C)}_n-\left(\begin{array}{c}W=X\\|\quad|\\Z-Y\end{array}\right)_o-\text{(C≡C)}_p-$$

wherein each of n, o, and p are integers ranging from 0 to 3 and the sum of n+o+p is at least 2, and wherein W, X, Y, and Z are independently carbon or nitrogen, as disclosed in U.S. Pat. Nos. 6,096,875 and 6,197,555, which are hereby incorporated herein by reference. Linkers comprising this structure are referred to herein as "rigid linkers." Additional moieties useful as linkers in the invention include, but are not limited to the following structures:

referred to herein as a "propargyl-ethyl-oxide-amino linker" or "EO linker";

referred to herein as a "propargyl-propyl-oxide-amino linker" or "PO linker";

referred to herein as a "propargyl linker" or "PA linker";

referred to herein as a "phosphate linker" or "P linker";

referred to herein as a "benzylamine linker" or "Bn Linker." The ring in benzylamine linkers may be substituted in a chemically reasonable manner.

Linker moieties useful in the invention include polymers of the above structures, for example, EO-Bn linkers, EO-P linkers, EO-P-Bn linkers, etc.

As used herein, the term "tuned linkers" refers to linkers that have altered hydrophobicity or hydrophilicity, for example, because of the addition of a side chain. Such linkers may be used, for example, to adjust the mobility of the dye-labeled ribonucleotides of the invention during polyacrylamide gel electrophoresis, to adjust the spectral properties of dye-labeled ribonucleotides, to minimize quenching, or to alter the emission maxima of dye-labeled ribonucleotides. By tuning the dye-labeled ribonucleotide analogs corresponding to rATP, rGTP, rCTP, and rUTP, 4-color sets of the compounds of the invention having improved relative electrophoretic mobility and peak height evenness are provided for use in DNA sequencing protocols.

As used herein, the term "heterocycle linker" refers to any linker that can form an intermolecular chelate, preferably 5 or 6-membered, with water or any metal and the respective nucleobase.

As used herein, the term "independently" means that the identity of each element is selected without regard to the identity of other elements and may be either the same or different from that of other elements.

As used herein, the term "multimer" refers to polymers of unit monomers, wherein the polymer may comprise monomers of a single type or of different types in any order or combination. Preferably, a multimer consists of 2 to 10 monomers.

In order to further aid the understanding of the invention, specific dye-labeled ribonucleotide analogs are referred to throughout the specification. These references are not, however, intended to limit the scope of the invention.

The dye-labeled ribonucleotides of the invention are compounds of the general formula:

wherein Dye is any reporter group, preferably selected from fluorescein-type dyes, rhodamine-type dyes, energy transfer dye pairs, and cyanine-type dyes;

wherein L is a linker, preferably a propargyl-ethyl-oxide-amino linker, a propargylamino linker, a propargyl-propyl-oxide-amino linker, a benzylamine linker, a phosphate linker, a rigid linker, a heterocycle linker, a tuned linker, or a multimer of these linkers;

wherein B is a nucleobase;

wherein $R_1$ and $R_2$ are independently H, OH, $NH_2$, or SH, preferably OH; and wherein $R_3$ is triphosphate, α-thiotri, or a salt thereof.

The dye-labeled ribonucleotides of the invention include pyrimidine-type compounds of the general formula I:

Formula I wherein X is N, NH, or C;

wherein Y is O or $NH_2$;

wherein $R_1$ and $R_2$ are independently H, OH, $NH_2$, or SH, preferably OH;

wherein $R_3$ is either triphosphate, α-thiotriphosphate, or a salt thereof;

wherein $L_1$ is a linker, preferably a propargyl-ethyl-oxide-amino linker, a propargylamino linker, a propargyl-propyl-oxide-amino linker, a benzylamine linker, a phosphate linker, a rigid linker, or a multimer of these linkers, more preferably either a propargyl-ethyl-oxide-amino linker or a propargylamino linker;

wherein $L_2$ is a benzylamine linker or a phosphate linker;

wherein n=0-4, m=0-4, and m+n is at least 1; and wherein the dye is any reporter group, preferably a rhodamine-type dye, a fluorescein-type dye, an energy transfer dye, or a cyanine-type dye.

The dye-labeled ribonucleotides of the invention also include purine-type compounds of the general formula II:

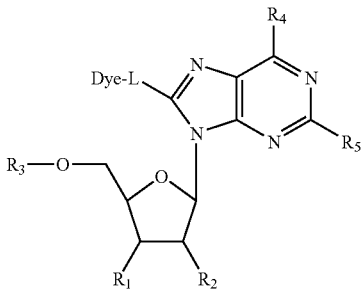

Formula II wherein L is a linker, preferably a propargyl-ethyl-oxide-amino linker, propargylamino linker, propargyl-propyl-oxide-amino linker, benzylamine linker, phosphate linker, or rigid linker, more preferably either a propargyl-ethyl-oxide-amino linker or a propargylamino linker;

wherein $R_4$ is either $NH_2$, OH, or O, and $R_5$ is either $NH_2$, OH, or H;

wherein $R_1$ and $R_2$ are independently H, OH, $NH_2$, or SH, preferably OH;

wherein $R_3$ is either triphosphate, α-thiotriphosphate, or a salt thereof; and wherein the dye is any reporter group, preferably a rhodamine-type dye, a fluorescein-type dye, an energy transfer dye, or a cyanine-type dye.

The dye-labeled ribonucleotides of the invention also include purine-type compounds of the general formula III:

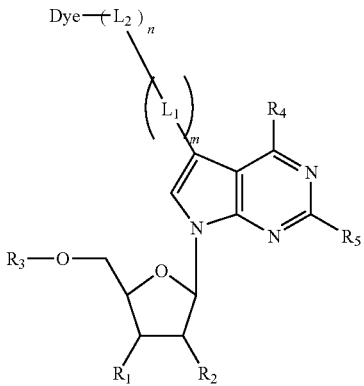

Formula III wherein $L_1$ is a linker, preferably a propargyl-ethyl-oxide-amino linker, propargylamino linker, propargyl-propyl-oxide-amino linker, benzylamine linker, phosphate linker, or rigid linker, more preferably either a propargyl-ethyl-oxide-amino linker or a propargylamino linker;

wherein $L_2$ is a benzylamine linker or a phosphate linker;

wherein n=0-4, m=0-4, and m+n is at least 1;

wherein $R_4$ is either $NH_2$, OH, or O, and $R_5$ is either $NH_2$, OH, or H;

wherein $R_1$ and $R_2$ are independently H, OH, $NH_2$, or SH, preferably OH;

wherein $R_3$ is either triphosphate, α-thiotriphosphate, or a salt thereof; and wherein the dye is any reporter group, preferably a rhodamine-type dye, a fluorescein-type dye, a energy transfer dye, or a cyanine-type dye.

In another embodiment, the dye-labeled ribonucleotides of the invention include purine-type compounds of the general formula IV:

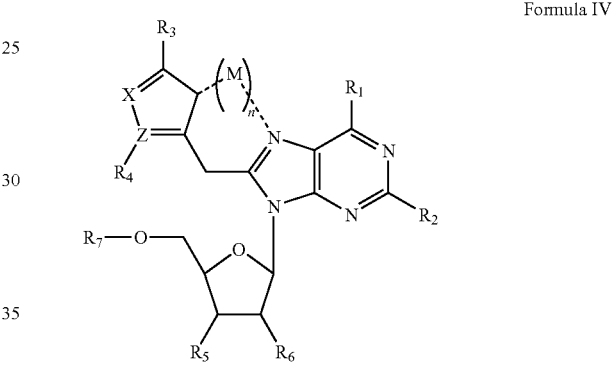

Formula IV wherein $R_1$, $R_2$, and $R_4$ are independently H, O, OR, S, SR, $NR_2$, or $CR_2$;

wherein $R_3$ is SR, $NR_2$, OR, or $CR_2$ and comprises a reporter group, preferably a rhodamine-type dye, a fluorescein-type dye, an energy transfer dye, or a cyanine-type dye;

wherein R is hydrogen, alkyl, preferably C1-C6 alkyl, C2-C6 alkenyl, or C2-C6 alkynyl, aryl, preferably benzyl substituted at from 0 to 3 positions in a chemically reasonable manner with F, Cl, Br, I, C1-C18 alkyl, Silyl, OH, OR', SH, SR', SOR', $SO_2R'$, $SO_3$, $NH_2$, NHR', or $NR'_2$, or an amino acid;

wherein $R_5$ and $R_6$ are independently H, OH, $NH_2$, or SH, preferably OH;

wherein $R_7$ is either triphosphate, α-thiotriphosphate, or a salt thereof;

wherein R' is OH, alkyl, preferably C1-C6 alkyl, or alkynyl, preferably C2-C6 alkynyl;

wherein X, Y, and Z are independently carbon, nitrogen, oxygen, sulfur, phosphorus, or selenium;

wherein n is 0 or 1; and wherein M is $H_2O$ or any metal, preferably a Group IA metal or a Group IIA metal, more preferably $Li^+$, $Na^+$, $K^+$, $Mg^{2+}$, or $Ca^{2+}$.

In formula IV, the linker moiety at C8 may be in the same plane as the purine or skewed to lie outside of the purine plane.

In another embodiment, the dye-labeled ribonucleotides of the invention include purine-type compounds of the general formula V:

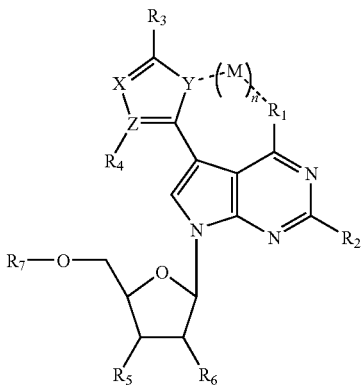

Formula V wherein $R_1$, $R_2$, and $R_4$ are independently H, O, OR, S, SR, $NR_2$, or $CR_2$, wherein $R_3$ is SR, $NR_2$, OR, or $CR_2$ and comprises a reporter group, preferably a rhodamine-type dye, a fluorescein-type dye, an energy transfer dye, or a cyanine dye;

wherein R is hydrogen, alkyl, preferably C1-C6 alkyl, C2-C6 alkenyl, or C2-C6 alkynyl, aryl, preferably benzyl substituted at from 0 to 3 positions in a chemically reasonable manner with F, Cl, Br, I, C1-C18 alkyl, Silyl, OH, OR', SH, SR', SOR', $SO_2R'$, $SO_3$, $NH_2$, NHR', or $NR'_2$, or an amino acid;

wherein $R_5$ and $R_6$ are independently H, OH, $NH_2$, or SH;

wherein $R_7$ is either triphosphate, α-thiotriphosphate, or a salt thereof;

wherein R' is OH, alkyl, preferably C1-C6 alkyl, or alkynyl, preferably C2-C6 alkynyl;

wherein X, Y, and Z are independently C, N, O, S, P, or Se;

wherein n is 0 or 1; and wherein M is $H_2O$ or any metal, preferably a Group IA metal or a Group IIA metal, more preferably $Li^+$, $Na^+$, $K^+$, $Mg^{2+}$, or $Ca^{2+}$.

In formula V, the linker moiety at C7 may be in the same plane as the purine or skewed to lie outside of the purine plane.

In another embodiment, the dye-labeled ribonucleotides of the invention include pyrimidine-type compounds of the general formula VI:

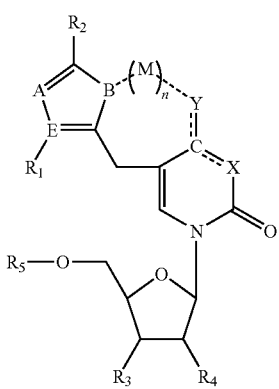

Formula VI wherein $R_1$ is H, O, OR, S, SR, $NR_2$, or $CR_2$, wherein $R_2$ is SR, $NR_2$, OR, or $CR_2$ and comprises a reporter group, preferably a rhodamine-type dye, a fluorescein-type dye, an energy transfer dye, or a cyanine dye;

wherein R is hydrogen, alkyl, preferably C1-C6 alkyl, C2-C6 alkenyl, or C2-C6 alkynyl, aryl, preferably benzyl substituted at from 0 to 3 positions in a chemically reasonable manner with F, Cl, Br, I, C1-C18 alkyl, Silyl, OH, OR', SH, SR', SOR', $SO_2R'$, $SO_3$, $NH_2$, NHR', or $NR'_2$, or an amino acid;

wherein $R_3$ and $R_4$ are independently H, OH, $NH_2$, or SH, preferably OH;

wherein $R_5$ is either triphosphate, α-thiotriphosphate, or a salt thereof;

wherein R' is OH, alkyl, preferably C1-C6 alkyl or C2-C6 alkynyl;

wherein X is N, NH, or C;

wherein Y is O or $NH_2$;

wherein A, B, and E are independently C, N, O, S, P, or Se;

wherein n is 0 or 1; and wherein M is $H_2O$ or any metal, preferably a Group IA metal or a Group IIA metal, more preferably $Li^+$, $Na^+$, $Mg^{2+}$, or $Ca^{2+}$.

In another embodiment, the dye-labeled ribonucleotides of the invention include purine-type compounds of the general formula VII:

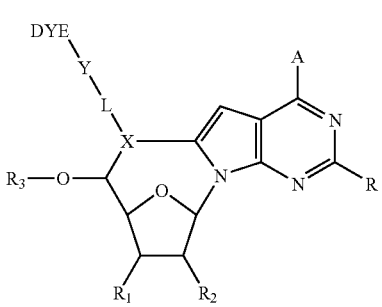

Formula VII wherein A is $NH_2$, OH, or O;

wherein R is H, O, $NH_2$, NHR', S, CHR', $CR'_2$, or halide, preferably iodide, bromide, chloride, or fluoride, more preferably chloride or fluoride;

wherein R' is hydrogen or alkyl, preferably C1-C7 alkyl;

wherein $R_1$ and $R_2$ are independently H, OH, $NH_2$, or SH, preferably OH;

wherein $R_3$ is either triphosphate, α-thiotriphosphate, or a salt thereof;

wherein L is alkyl, preferably C1-C20 alkyl, C2-C20 alkenyl, or C2-C20 alkynyl, or aryl substituted at from 0 to 3 positions in a chemically reasonable manner with F, Cl, Br, I, C1-C18 alkyl, Silyl, OH, OR', SH, SR', SOR', $SO_2R'$, $SO_3$, or $NR'_2$;

wherein X is CR or N and Y is O, S, or NH; and wherein the dye is any reporter group, preferably a rhodamine-type dye, a fluorescein-type dye, an energy transfer dye, or a cyanine dye.

The electrophoretic mobility and incorporation of dye labeled ribonucleotides according to formula VII may be "tuned" by adding functional groups to the linker moiety between "X" and the dye.

The dye-labeled ribonucleotides of the invention also include pyrimidine-type compounds of the general formula VIII:

Formula VIII

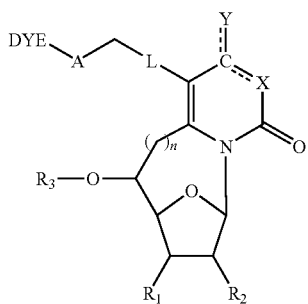

wherein X is N, NH, or C;
wherein Y is O or NH$_2$;
wherein R$_1$ and R$_2$ are independently H, OH, NH$_2$, or SH, preferably OH;
wherein R$_3$ is either triphosphate, α-thiotriphosphate, or a salt thereof;
wherein A is O, S, or NH;
wherein L is alkyl, preferably C1-C20 alkyl, C2-C20 alkenyl, or C2-C20 alkynyl, or aryl substituted at from 0 to 3 positions in a chemically reasonable manner with F, Cl, Br, I, C1-C18 alkyl, Silyl, OH, OR', SH, SR', SOR', SO$_2$R', SO$_3$, or NR'$_2$;
wherein R' is hydrogen or alkyl, preferably C1-C7 alkyl;
wherein n is 1 to 10; and
wherein the dye is any reporter group, preferably a rhodamine-type dye, a fluorescein-type dye, an energy transfer dye, or a cyanine-type dye.

The dye-labeled ribonucleotides of the invention also include purine-type compounds of the general formula IX:

Formula IX

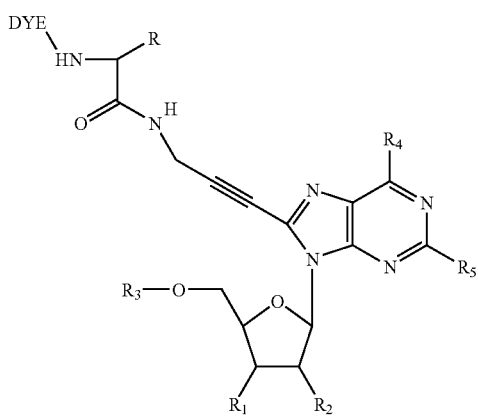

wherein R$_4$ is NH$_2$, OH, or O and R$_5$ is NH$_2$, OH, or H, provided that if R$_4$ is NH$_2$, R$_5$ is H and if R$_4$ is O, R$_5$ is NH$_2$;
wherein R$_1$ and R$_2$ are independently H, OH, NH$_2$, or SH, preferably OH;
wherein R$_3$ is either triphosphate, α-thiotriphosphate, or a salt thereof;
wherein the dye is any reporter group, preferably a rhodamine-type dye, a fluorescein-type dye, a big-dye, or cyanine dyes, and
wherein R is a side chain for mobility tuning.

The dye-labeled ribonucleotides of the invention also include pyrimidine-type compounds of the general formula X:

Formula X

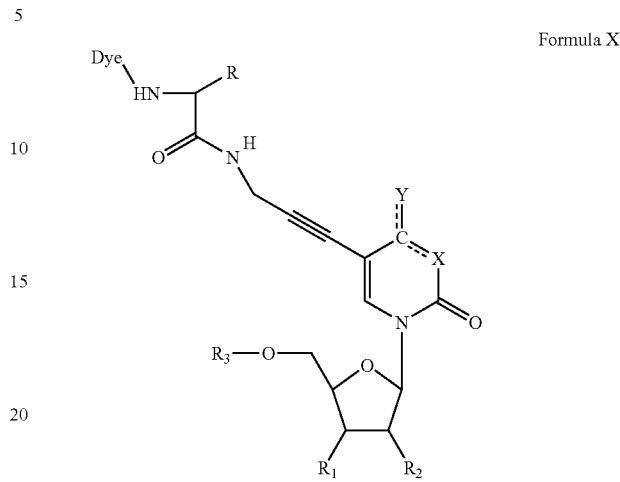

wherein X is N, NH, or C;
wherein Y is O or NH$_2$;
wherein R$_1$ and R$_2$ are independently H, OH, NH$_2$, or SH, preferably OH;
wherein R$_3$ is either triphosphate, α-thiotriphosphate, or a salt thereof;
wherein the dye is any reporter group, preferably a rhodamine-type dye, a fluorescein-type dye, a big-dye, or cyanine dyes, and
wherein R is a side chain for mobility tuning.

Those of skill in the art will appreciate that many of the compounds encompassed by the structures herein may exhibit the phenomena of tautomerism, conformational isomerism, geometric isomerism and/or stereoisomerism. As the formulae drawings within this specification and claims can represent only one of the possible tautomeric, conformational isomeric, enantiomeric or geometric isomeric forms, it should be understood that the invention encompasses any tautomeric, conformational isomeric, enantiomeric and/or geometric isomeric forms of the compounds having one or more of the utilities described herein. As the nomenclature corresponds to the illustrated structural formulae, which represent only one of several possible tautomeric forms (or resonance structures) of the compounds, it will be understood that these references are for convenience only, and that any such references are not intended to limit the scope of the compounds described herein.

In addition, those of skill in the art also will recognize that the compounds of the invention may exist in many different protonation states, depending on, among other things, the pH of their environment. While the structural formulae provided herein depict the compounds in only one of several possible protonation states, it will be understood that these structures are illustrative only, and that the invention is not limited to any particular protonation state—any and all protonated forms of the compounds are intended to fall within the scope of the invention.

The compounds of the invention may bear multiple positive or negative charges. Typically, the net charge of the labeled ribonucleotides of the invention will be negative. The associated counter ions are typically dictated by the synthesis and/or isolation methods by which the compounds are obtained. Typical counter ions include, but are not limited to, ammonium, sodium, potassium, lithium, halides, acetate, trifluoroacetate, etc., and mixtures thereof. It will be understood that the identity of any associated counter ion is not a critical feature of the invention, and that the invention encompasses the compounds in association with any type of counter ion. Moreover, as the compounds can exists in a variety of different forms, the invention is intended to encompass not only forms that are in association with counter ions (e.g., dry salts), but also forms that are not in association with counter ions (e.g., aqueous or organic solutions).

The dye-labeled ribonucleotides of the invention are useful substrates for DNA sequencing. As previously described, chain termination methods generally require template-dependent primer extension in the presence of chain-terminating nucleotides, resulting in a distribution of partial fragments which are subsequently separated by size. Standard dideoxy sequencing methods utilize dideoxynucleoside triphosphates for chain termination and a DNA polymerase such as the Klenow fragment of E. coli DNA polymerase I. See Sanger et al., supra.

Unlike the incorporation of a ddNTP, the incorporation of a dye-labeled ribonucleotide according to the invention does not result in a chain termination event. Rather, a DNA sequencing reaction comprising both dye-labeled rNTPs and dNTPs produces a mixture of full-length primer extension products randomly substituted with rNTPs, which are susceptible to cleavage at the 3'-5' phosphodiester linkage between a ribo- and an adjacent deoxyribonucleotide. Such primer extension products provide an alternative to ddNTP-terminated extension products for the generation of sequence information. Following primer extension in the presence of a single rNTP (e.g., rATP, rGTP, rCTP, or rUTP), the reaction mix can be treated with either alkali, heat, a ribonuclease or other means for hydrolyzing the extension products at each occurrence of the ribonucleotide to generate a series of extension products each with a dye-labeled 3'-ribonucleotide terminus. For a given target, analysis of the resulting sequencing products provides a sequencing ladder, i.e., a series of identifiable signals in the G, A, T, and C lanes corresponding to the nucleic acid sequence of the target. The resulting sequencing ladder provides comparable information whether the method utilizes ddNTPs or dye-labeled rNTPs.

When the DNA polymerase used in a sequencing reaction is a modified thermostable polymerase, such as those described in U.S. Pat. No. 5,939,292, the dye-labeled ribonucleotides of the invention are useful substrates for direct PCR sequencing (cycle sequencing). Because, in contrast to the incorporation of ddNTPs, the incorporation of dye-labeled ribonucleotides does not cause chain termination, the invention provides a method for the exponential amplification of target DNA sequences by PCR. The invention, thus, provides greater sensitivity over currently available methods for cycle sequencing and allows the nucleotide sequence of a target to be determined from a small number of template molecules.

DNA sequencing by PCR using the dye-labeled ribonucleotides of the invention involves (i) annealing an oligonucleotide primer to a template; (ii) extending the primer with a DNA polymerase that can incorporate both dNTPs and rNTPs in a reaction comprising a mixture of unlabeled dNTPs and at least one dye-labeled ribonucleotide of the invention, (iii) treating the resulting primer extension products with either alkali, heat, a ribonuclease, or other means for hydrolyzing the extension products at each occurrence of a ribonucleotide (each cleavage at the 3'-5' phosphodiester linkage between a ribo- and an adjacent deoxyribonucleotide results in a primer extension product that is labeled at the 3'-end), (iv) optionally, separating the resulting fragments that contain the primer from other fragments, (v) resolving the primer-containing extension products by means of, for example, high-resolution denaturing polyacrylamide/urea gel electrophoresis, capillary separation, or other resolving means; and (vi) detecting the fragments, for example, using a scanning spectrophotometer or fluorometer.

Methods for separating extension products that contain the primer from other hydrolysis products will be apparent to those of skill in the art. Suitable methods include, but are not limited to, using biotinylated primers, which can be separated from other cleavage products using, for example, avidin beads, or using hybridization based pull-out (HBP), wherein extension products containing the sequencing primers are separated from other nucleic acids in the mixture using complementary polynucleotides or oligonucleotides as described in U.S. Pat. No. 6,124,092 to O'Neill et al., which is hereby incorporated herein by reference in its entirety. It will be apparent to the skilled artisan that if primers complementary to both strands of a double-stranded template are included in the reaction and those primers can be separated, not only from the other cleavage products in the reaction, but also from each other, then the sequence of both strands of a DNA template can be determined in one reaction.

It also will be apparent to the skilled artisan that using a set of four ribonucleotides of the invention each comprising a different dye label enables one to determine the sequence of one or both strands of a DNA template in a single reaction. The invention thus includes four color sets of dye-labeled ribonucleotides that are characterized by equivalent electrophoretic mobility and peak height evenness. The mobility of each member of such four color sets may be adjusted by, for example, the choice between propargyl-ethyl-oxide-amino and propargylamino linkers, the choice between rigid and floppy linkers, and by including hydrophobic or hydrophilic amino acid side chains in the linker. An exemplary set of the dye-labeled ribonucleotides of the invention comprises rATP-PA-5-R6G, rCTP-PA-6-Rox, rUTP-PA-6-TAMRA, and rGTP-EO-5-R110.

The invention also encompasses methods for detecting mutations, including, but not limited to SNPs, in DNA by using pairs of oligonucleotide primers selected to give a small amplicon containing a mixture of dNTPs and dye-labeled rNTPs. In this aspect of the invention, two primers and a DNA polymerase that can incorporate both dNTPs and rNTPs are used to amplify a small segment of template DNA. The resulting amplicon is a chimeric DNA/dye-labeled RNA molecule, which can be cleaved using alkali, heat, a ribonuclease, or other means for hydrolyzing the 3'-5' phosphodiester linkage between a ribo- and an adjacent deoxyribonucleotide, leaving a single dye-labeled ribonucleotide on the 5' fragment. The resulting mixture is separated by, for example, electrophoresis through a denaturing acrylamide or dialkylacrylamide matrix to give a specific microsequence in which the presence or absence of the mutation can be unambiguously determined.

A general scheme for this method is illustrated in FIG. 1. In FIG. 1, a small segment of genomic DNA is amplified using two primers of different length in the presence of dNTP's and a set of four dye-labeled ribonucleotides according to the invention. In this example, Primer A is 23 bp long and primer B is 21 bp long. The position of the mutation of interest is preferably, but does not have to be, the first nucleotide located 3' to one, or both, of the primers. In this example, the SNP is the first base 5' to each primer. During the PCR reaction, dye-labeled ribonucleotides, represented by the vertical ticks in the amplicon in FIG. 1, are incorporated along with the deoxynucleotides. The incorporation of the dye-labeled ribonucleotides does not stop the polymerization reaction, which can therefore go on to the other extremity of the template. The strand produced, therefore, will contain a priming site for the other primer and can be a template in the following cycles of the PCR reaction.

The resulting amplicons are hydrolyzed, for example, in the presence of NaOH to break them at every position where a dye-labeled ribonucleotide was incorporated to produce a set of fragments each of which has one of the four ribonucleotides at its 3' extremity. The extension products from Primer A range from 24 to 44 bases in length. The extension products from Primer B range from 22 to 44 bases in length. These products are separated on a denaturing matrix, in this example on a 16% acrylamide gel.

Figure 2:
FIG. 2 shows a method for detecting a SNP on both strands of DNA template simultaneously when one primer is longer than the other primer.
Figure 2:
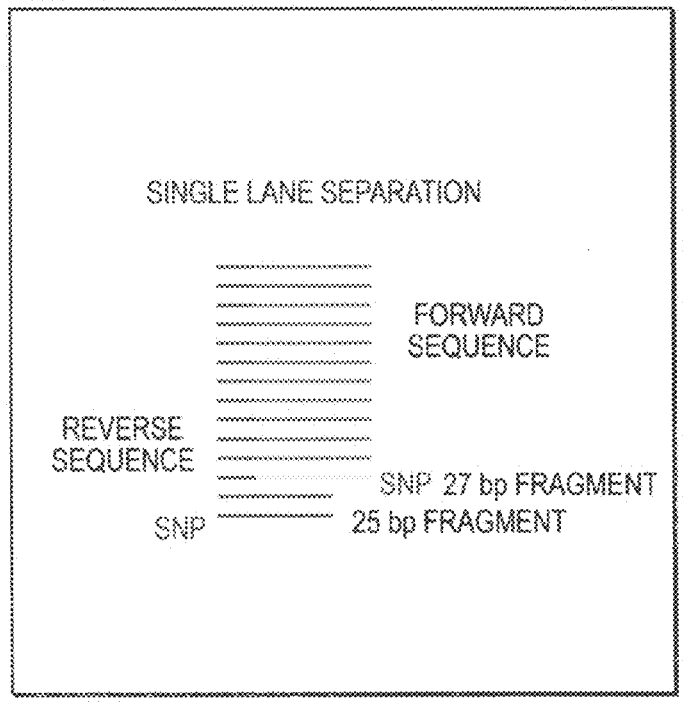

The electrophoresis results are illustrated in FIG. 2. Because Primer C is shorter than Primer D, the smallest fragments result from the extension of Primer C. Because the SNP is located immediately adjacent to the 3'-end of Primer C, which is 24 nucleotides long, the smallest fragment detected, which is 25 nucleotides long, corresponds to the SNP.

Figure 3:
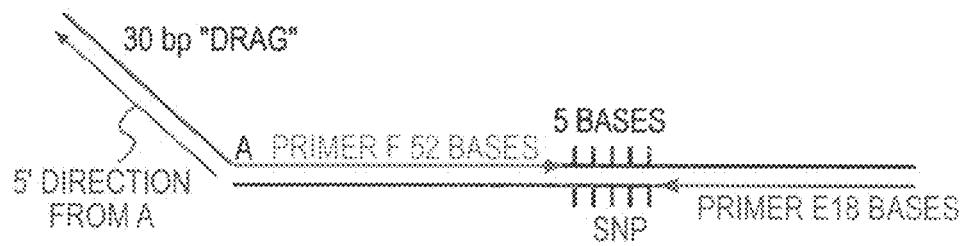
FIG. 3 shows a method for detecting a SNP on both strands of a DNA template simultaneously using one primer with a modified base that will not permit extension in the 5' direction from point A.
Figure 3:
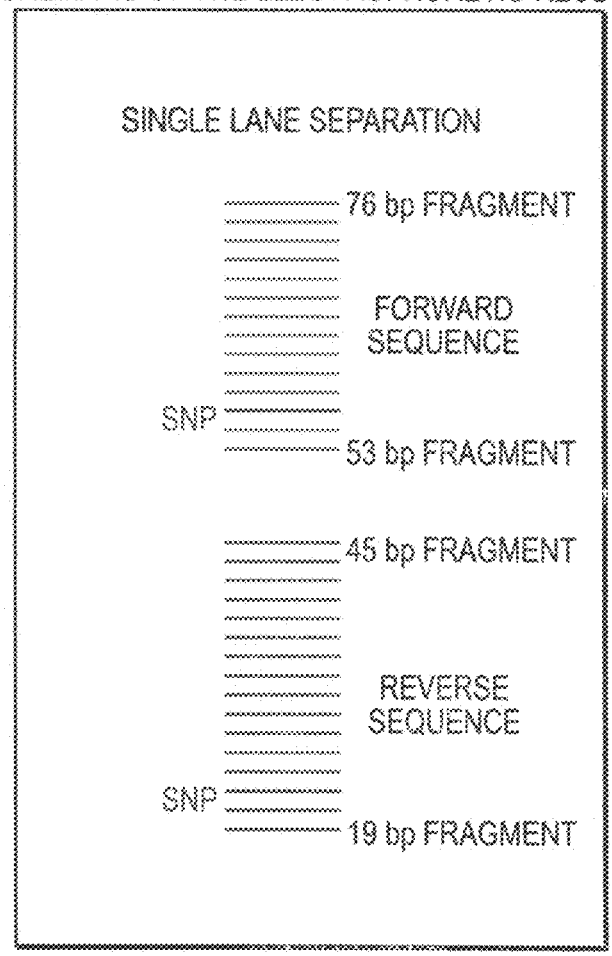

FIG. 3 illustrates another embodiment of the invention, In this method, the microsequence (i.e., the partial sequence between the two primers) of both template strands is determined using primers of unequal mobility. In FIG. 3, one of the two primers, Primer F, is longer of than the other primer and contains a modified base "A" that does not permit extension in the 5' direction, and that preferably, but not necessarily, is located midway along the primer sequence. In FIG. 3, Primer E, which is 18 nucleotides long, and Primer F, which is 52 nucleotides long, are used to amplify a 5 bp portion of genomic DNA in the presence of dNTPs and a set of dye-labeled rNTPs according to the invention. After the resulting amplicons are cleaved using NaOH, labeled extension products of Primer E will range from 19 to 45 nucleotides in length because Primer E cannot be extended beyond modified base A of Primer F. The labeled extension products of Primer F will range from 53 to 76 nucleotides in length and do not overlap with the Primer E fragments. After the mixture of dye-labeled fragments is resolved by electrophoresis through a denaturing matrix, the SNP which corresponds to the 21 nucleotide fragment of Primer E on the reverse strand and the 55 nucleotide fragment of Primer F on the forward strand, can be unambiguously identified on both strands because the microsequences do not overlap. As alternatives to the use of a longer primer comprising a modified base, the method exemplified in FIG. 3 can also be practiced using one primer comprising, for example, polyethylene glycol or amino acids at its 5'-end.

Figure 4:
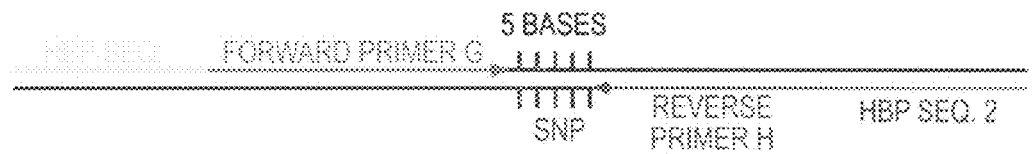
FIG. 4 shows a method for detecting a SNP on both strands of a DNA template simultaneously using hybridization based pull-out (HBP) primers.
Figure 4:
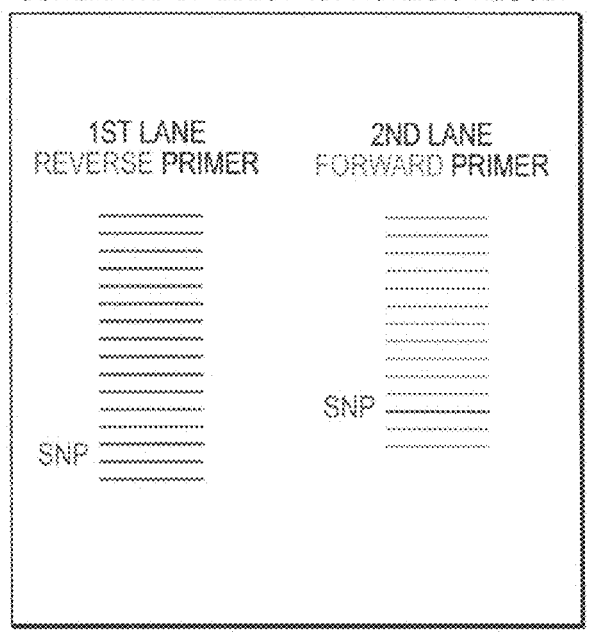

In another embodiment of the invention, which is illustrated in FIG. 4, the extension products from each primer are separated prior to analysis, for example, using HBP, as shown, or biotinylated oligonucleotides, permitting the microsequence of both template strands to be unambiguously determined after electrophoresis in two lanes of a denaturing matrix.

The dye-labeled ribonucleotides of the invention have other uses, which will be apparent to one of skill in the art. For example, primer extension products comprising a mixture of dNTPs and dye-labeled ribonucleotides may be cleaved by any of the methods described above to yield dye-labeled polynucleotide random fragments, which are useful as hybridization probes. The compounds of the invention also permit the synthesis of dye-labeled RNAs, which are useful, for example, in quantifying the yield from an in vitro RNA synthesis and for preparing antisense and/or sense probes for in situ hybridization. The skilled artisan will appreciate additional uses for the dye-labeled ribonucleotides of the invention from the examples below Reference will now be made in detail to the exemplary embodiments of the invention, examples of which are illustrated below.

Example 1

General Procedures: Sure Seal™ (Aldrich) or Puriss (Fluka) solvents were used for reactions requiring anhydrous conditions. All reactions were carried out under a positive argon or nitrogen atmosphere unless otherwise noted. Reagents were added at room temperature unless otherwise noted. Dyes obtained from manufacturing are activated as N-hydroxysuccinamide (NHS) esters and formulated to 5 mg per 60 μL dimethylsulfoxide (DMSO). Thin layer chromatography (TLC) was performed on silica gel $GHLF_{254}$ 250 μm plates (Analtech).

Analytical reverse phase (RP) high performance liquid chromatography (HPLC) was performed with a PE series 250 Binary LC pump interfaced with a PE 783A absorbance detector set at a wavelength λ 260 nm. For method A, a Spheri-5 RP-18, 5 μm, 4.6×100 mm column was used with a linear gradient of 0-50% acetonitrile (AcCN) over 20 min, and a flow of 1 mL/min with 0.1 M triethylammonium bicarbonate (TEAB) as buffer unless otherwise noted.

For purification by ion exchange, HPLC was performed on a PE series 410 B10 LC pump interfaced with a PE 785A absorbance detector (λ 260 nm) and a PE LC 240 fluorescence detector set at emission and absorbance values appropriate to the respective dye system. The column was developed with a linear gradient of 0-100% 0.1 M TEAB-1.5 M TEAB, 40% AcCN over 20 min at a flow rate of 1.5 mL/min. For two step purification methods ion exchange chromatography was followed by RP-C8 HPLC on a PE RP-8, 5 μm 4.6×220 mm column with a linear gradient of 0-50% AcCN over 15 min at a flow rate of 1 mL/min with 0.1 M TEAB as the buffer unless otherwise noted.

Preparatory reverse phase HPLC (Prep-HPLC) was performed on a Waters PrepLC 4000 system with a 40×450 mm RP-18 column using a linear gradient of 5-50% AcCN over 20 min, flow-rate 50 mL/min with 0.1 M TEAAc buffer unless otherwise indicated (Method C)

Nuclear Magnetic Resonance spectra (NMR, $^1H$, $^{31}P$, $^{19}F$, $^{13}C$) were recorded on a Varian XL300 NMR spectrometer. Low resolution mass spectra (LRMS) were performed on a PE SCIEX AP-100 Electrospray Mass spectrometer. Absorbance measurements were performed on a Perkin-Elmer Lambda-Bio UV-Vis spectrophotometer.

Example 2

Synthesis of 7-Deaza-7-iodoadenosine

Heterocycle preparation exemplified for 6-chloro-7-iodo-pyrrolo[2,3-d]pyrimidine (6-chloro-7-deaza-7-iodopurine). See Seela, F et al., Helv. Chim. Acta, 73: 1602 (1990); Davol, J., J. Chem. Soc., 131 (1960); Wellcome Foundation, B. P. 812,366 (Apr. 22, 1959).

The synthesis of 6-chloro-7-deaza-7-iodopurine 3.

Scheme I

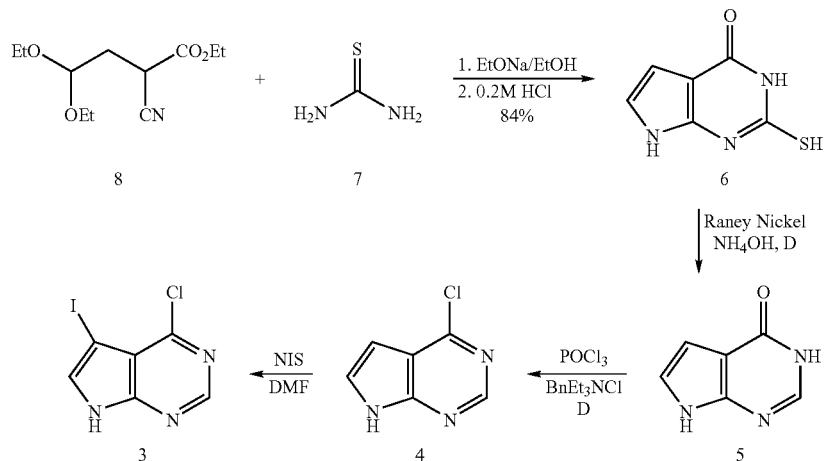

Hilbert-Johnson Glycosylation Method.

Reference: Townsend et al., Nucleosides & Nucleotides 18: 153 (1999) and references therein.

Scheme II

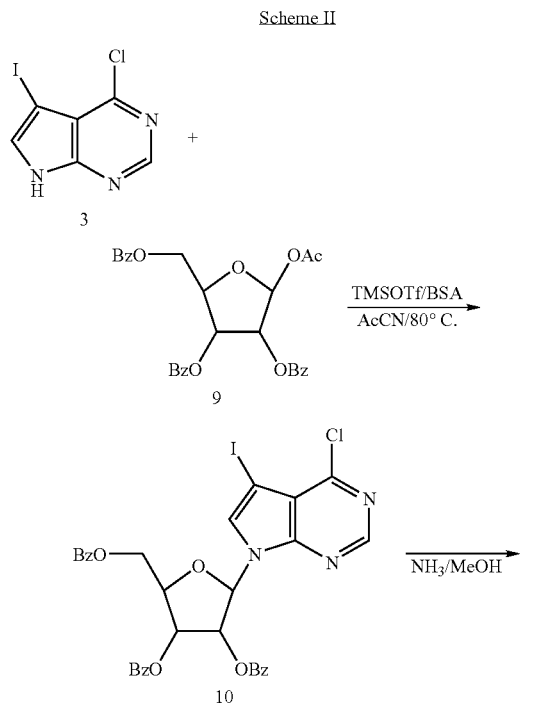

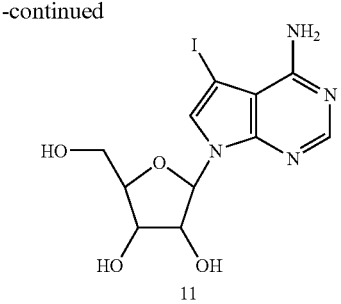

Preparation of 10: N,O-Bis(trimethylsilyl)acetamide (BSA, 1.8 mL. 7.2 mmol) was added to a stirring suspension of 3 (2 g, 7.3 mmol) in dry acetonitrile (AcCN, 50 mL) at room temperature. After stirring for 10 min, 1-O-acetyl-2,3,5-tri-O-benzoyl-β-D-ribofuranose 9 (Aldrich, 3.6 g, 7.2 mmol) was added, followed by the addition of trimethylsilyl trifluoromethanesulfonate (TMSOTf, 2.6 mL, 14.4 mmol) via syringe. After stirring for 10 min, the reaction mixture was placed in an oil bath pre-heated to 80° C. and stirred at 80° C. for an additional 1 h. The reaction mixture was cooled to room temperature and then diluted with ethylacetate (EtOAc, 200 mL) and saturated sodium bicarbonate (NaHCO₃, 10 mL). The organic portion was washed successively with saturated NaHCO₃ (1×50 mL), water (1×50 mL), and saturated sodium chloride (1×50 mL), dried, and concentrated to give 5.7 g of crude 10 as a brown foam. The crude material was dissolved in EtOAc (40 mL) and filtered by suction through a pre-moistened (EtOAc) plug of silica gel (150 g), rinsing with hexanes/EtOAc (4/1, 500 mL). The filtrate was concentrated to give 2.7 g of 10 (64%) as a yellow foam.

Preparation of 11: Ammonia gas was vigorously bubbled through a suspension of 10 (2.7 g, 3.7 mmol) in methanol (MeOH, 80 mL) at 0° C. over a period of 30 min. The reaction mixture was sealed in a glass-lined steel bomb and heated to 100° C. for 20 h. The reaction vessel was cooled to 0° C., opened, and concentrated to give 2.7 g of a crude dark brown oil. This material was recrystallized from water to give 0.58 g, 40% of 11 as a tan solid.

Example 3

Synthesis of 7-iodoguanosine (16)

Reference: Ramasamy, et al., J. Heterocyclic Chem. 25: 1893 (1988).

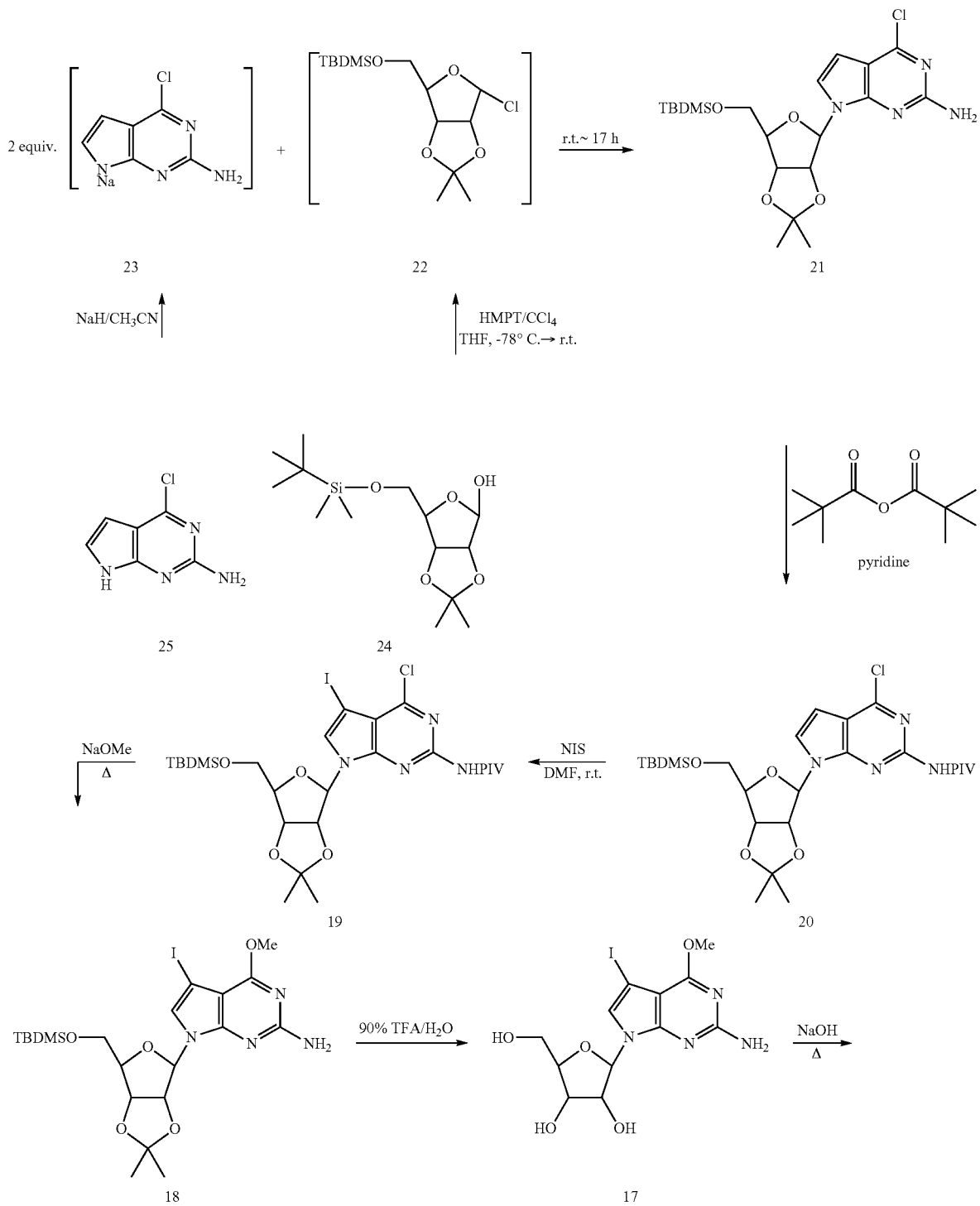

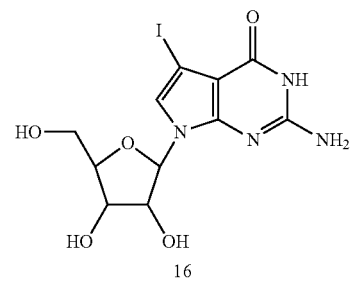

16

Preparation of 21: To a stirring solution of ribose sugar 24 [Kaskar et al., Synthesis, 1031 (1990)] (3.0 g, 10 mmol) dissolved in anhydrous THF (30 mL) and carbon tetrachloride ($CCl_4$, 1.2 mL, 12 mmol) cooled to −78° C. was added hexamethylphosphorus triamide (HMPT, 2.2 mL, 12 mmol). The resulting solution was stirred at −78° C. until it had formed a colorless gel and then allowed to warm to room temperature over a period of 1 h. The resulting solution of 22 was added to a stirring solution of 23 (20 mmol) in $CH_3CN$ (200 mL) at room temperature, and the reaction mixture was stirred for 17 h. The reaction mixture then was concentrated followed by dilution with water (100 mL). The aqueous solution was extracted with ethyl acetate (2×100 mL). The combined organic portions were washed with water (2×50 mL) and saturated NaCl (2×50 mL), dried over $MgSO_4$, and concentrated to give a dark brown oil. The crude oil was suspended in EtOAc/hexanes (1:4, 100 mL) and the resulting precipitate was filtered by suction washing with EtOAc/hexanes (1:4, 100 mL). Concentration of the filtrate afforded 4.8 g of a dark brown oil. Purification of this oil via column chromatography (silica gel, 500 g, EtOAc/hexanes, 1:4 as eluent) gave 1.85 g (41%) of 21 as a pale yellow solid.

Preparation of 20: To a stirring solution of 21 (1.5 g, 3.2 mmol) in pyridine (20 mL) was added trimethylacetyl chloride (520 μL, 4.2 mmol) and the reaction mixture was stirred at room temperature for 17 h. The reaction mixture was then taken up in 2:1 EtOAc/saturated sodium bicarbonate (75 mL) and stirred for an additional 2 h. The organic portion was dried over MgSO4 and concentrated to give 1.74 g of 20 as a brown foam. Crude 20 was taken up in 9:1 hexanes/EtOAc (10 mL), filtered through a plug of silica gel (30 g, pre-moistened with 9:1 hexanes/EtOAc), and rinsed with 9:1 hexanes/EtOAc (500 mL). Concentration of the filtrate gave 1.69 g (94%) of 20 as a colorless foam which was used without further purification in the next step.

Preparation of 19: To a stirring solution of 20 (1.6 g, 2.9 mmol) in DMF (15 mL) was added N-iodosuccinamide (NIS, 0.8 g, 3.2 mmol) and the reaction mixture was stirred in the dark for 17 h. $^1H$ NMR showed a 7:1 mixture of 20:19 at which time a second equivalent of NIS (0.8 g) was added to the reaction mixture. After 4 h, the reaction was analyzed by $^1H$ NMR to show a 1.6:1 mixture of 20:19. The reaction mixture was warmed to 45° C. and stirred for an additional 17 h. $^1H$ NMR showed no change in the ratio of product to starting material from the previous analysis. The reaction was quenched by adding saturated sodium bicarbonate (25 mL) and extracted with EtOAc (200 mL). The organic portion was washed with 5% sodium bisulfite (1×20 mL), water (2×25 mL), and saturated NaCl (2×25 mL), dried over $MgSO_4$, and concentrated to dryness to give 1.25 g of 20 and 19. This material again was dissolved in DMF (10 mL) followed by the addition of NIS (0.8 g) and the reaction mixture was allowed to stir for 17 h. $^1H$ NMR showed approximately 1:1 19:20. More NIS (0.8 g) was added to the mixture, which was analyzed as before after 8 h showing 2.3:1 19:20. Another equivalent of NIS (0.8 g) was added and the reaction mixture was stirred overnight. $^1H$ NMR showed the reaction was complete. The reaction mixture was quenched, extracted, dried as before, and filtered through a pre-moistened plug of silica gel (30 g, 4/1 hexanes/EtOAc, rinsing with 4:1 hexanes/EtOAc (150 mL)). Concentration afforded 1.29 g of 19 (67%) of suitable quality for the next step.

Preparation of 18: 19 (0.58 g, 0.87 mmol) was dissolved in freshly prepared sodium methoxide (NaOMe, 1 M, 25 mL) and heated to reflux for 1 h. The solution was cooled to 0° C. and the pH was adjusted to 6 with acetic acid (6 M). The solution was concentrated to dryness, suspended in EtOAc/hexanes (1:1, 10 mL), and filtered through a plug of silica gel (30 g, rinsing with EtOAc/hexanes (1:1, 250 mL). Concentration of the filtrate gave 0.32 g (64%) of 18 as a colorless foam of suitable quality for the next step.

Preparation of 17: An ice cold solution of trifluoroacetic acid/water (95:5, 10 mL) was added to 18 (0.32 g, 0.56 mmol) with stirring. The solution was stirred at 0° C. for 0.5 h. The reaction mixture was concentrated to dryness (co-evaporating with methanol (3×50 mL, to remove TFA)) and recrystallized with acetone/MeOH/DCM (5:2:4, 10 mL) to give 228 mg (97%) of 17 as a white powder.

Preparation of 16: A suspension of 17 (150 mg, 0.36 mmol) in NaOH (2 M, 10 mL) was heated to reflux for 2 h. The solution was cooled to 0° C. and neutralized with acetic acid (AcOH, 2 M). 16 was collected by filtration, washed with water, and dried to give 105 mg (72%) of 16 as a tan solid.

Example 4

Preparation of Linkers

Synthesis of 3-Ethoxy-[2'-N-Trifluoroacetamido-]-1-Propyne (EO-Linker) 28: NaH (60% dispersion in mineral oil, 22 g, 0.55 mol) was placed in a 1 L RB flask, rinsed with dry THF (50 mL), and suspended in THF (150 mL). The suspension was cooled to 0° C., followed by the dropwise addition of 2-aminoethanol (32 mL, 0.5 mol) with stirring over a period of 0.5 h. The reaction mixture was diluted with additional THF (500 mL) and allowed to warm to room temperature over a period of 2 h. The resulting solution was cooled to 0° C., followed by the slow addition of propargyl bromide (45 mL, 0.5 mol) over a period of 0.5-1 h. The reaction mixture was allowed to gradually warm to room temperature and stirred for 17 h. The reaction mixture was filtered by suction, rinsing with THF (100 mL), concentrated to a black syrup, and distilled by vacuum (6 mmHg, 35-42° C.) to give 17 g of desired amine 28'. 28' was added to ethyltrifluoroacetate (30 g, 0.21 mol) at 0° C. over a period of 0.5 h, followed by stirring at room temperature for 2 h. The reaction mixture was concentrated and distilled by vacuum (92-93° C., 6-7 mm Hg). This was repeated twice to give 15 g of 28 of suitable purity for the next step.

Synthesis of N-3-trifluoroacetamido-1-propyne (PA-Linker) 27. See Hobbs, Jr. et al., U.S. Pat. Nos. 5,047,519 and 5,151,507.

Example 5

Linker Coupling: See Hobbs, Jr. et al., U.S. Pat. No. 5,047,519.

Ribo-Adenosine PA, EO-Linker Coupling: Preparation of 1a and 1e

Scheme IV

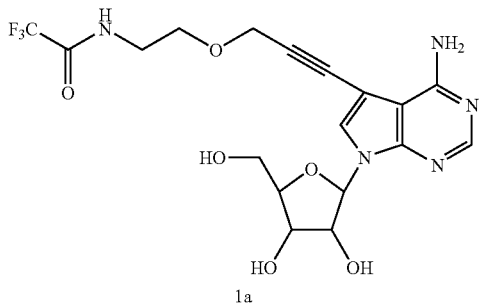

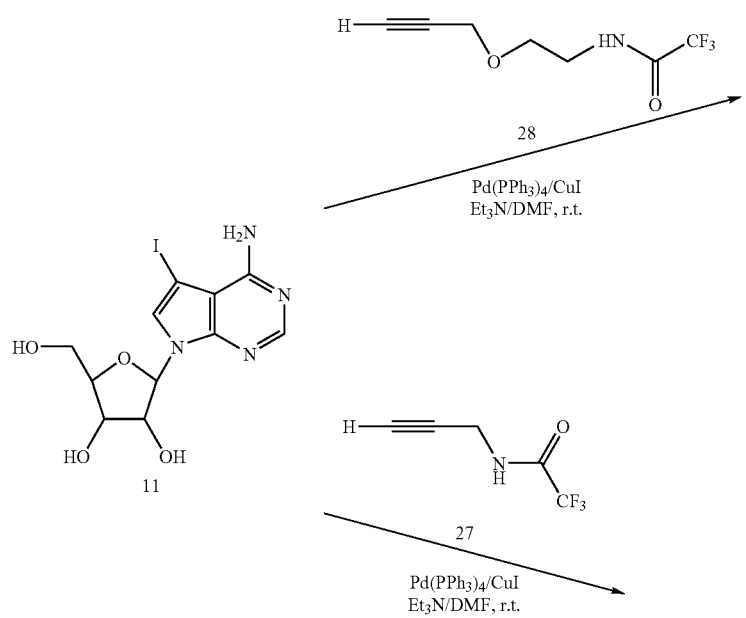

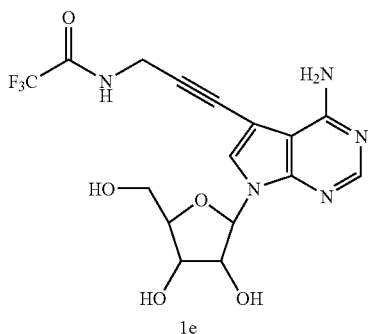

Preparation of 1a: To a stirring solution of 11 (100 mg, 0.25 mmol) in N,N-dimethylformamide (DMF, 4 mL) was added in the following order N-3-trifluoroacetamido-1-propyne 27 (PA-linker, 190 μL, 1.25 mmol), triethylamine, (TEA, 110 μL, 0.76 mmol), cuprous iodide (CuI, 10 mg, 0.05 mmol), and tetrakis(triphenylphosphine)palladium (30 mg, 0.025 mmol). The reaction mixture was stirred for 17 h and then quenched by the addition of Dowex-1 carbonate form (3 g) and rinsed with dichloromethane(DCM)/MeOH (1:1, 200 mL). The filtrate was concentrated and the crude product was purified by column chromatography [silica gel, 50 g, eluting with DCM/MeOH (9:1, 200 mL) followed by DCM/MeOH (8:2, 200 mL)] to give 84 mg of 2 as a brown solid.

Preparation of 1e: To a stirring solution of 11 (100 mg, 0.26 mmol) in DMF (1 mL) was added in the following order 3-ethyloxy-[2'-N-trifluoroacetamido-]-1-propyne 28 (EO-linker, 140 μL, 0.76 mmol), TEA (110 μL, 0.76 mmol), CuI (10 mg, 0.05 mmol), and tetrakis(triphenylphosphine)palladium (30 mg, 0.025 mmol). The reaction mixture was allowed to stir for 17 h followed by quenching with Dowex-1 carbonate form (3 g). The reaction mixture was filtered over a plug of celite (10 g) and rinsed with DCM/MeOH (1:1, 100 mL). The filtrate was concentrated and the crude product was purified by column chromatography [silica gel, 50 g, eluting with DCM/MeOH (9:1, 200 mL)] to give 90 mg of 1e (71%) as a brown solid.

Preparation of 2a and 2e: See Hobbs, Jr. et al., U.S. Pat. Nos. 5,047,519 and 5,151,507.

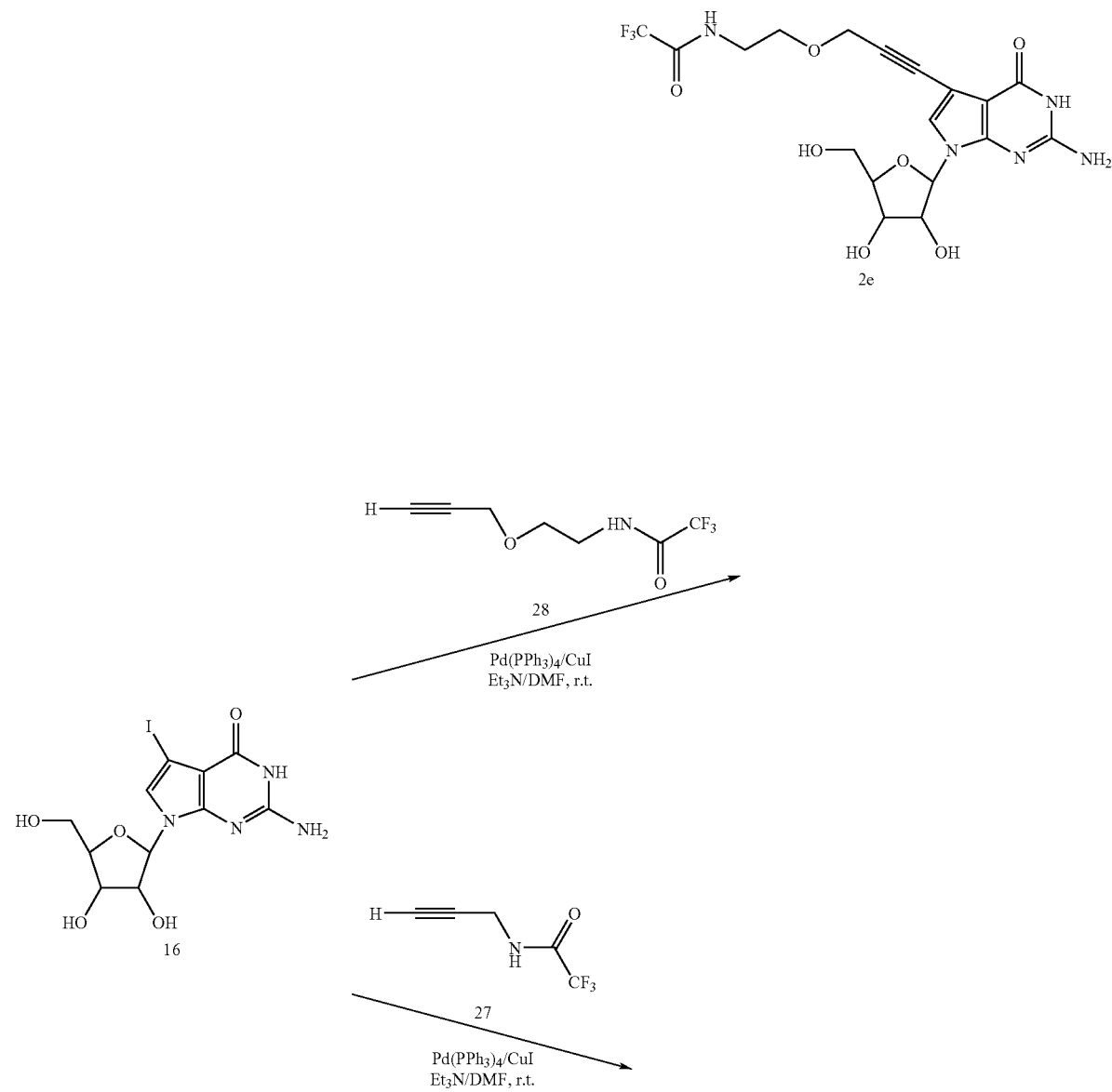

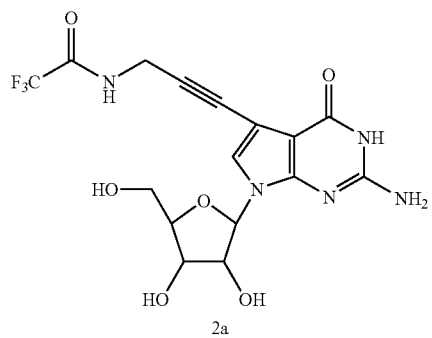

2a

Preparation of 2a: To a solution of 16 (50 mg, 0.12 mmol) in dry DMF (2 mL) at room temperature was added 27 (100 µL, 0.61 mmol), cuprous iodide (CuI, 8 mg, 0.04 mmol), tetrakis(triphenylphosphine)palladium(0) (14 mg, 0.012 mmol), and Et$_3$N (50 µL, 0.37 mmol). The reaction mixture was stirred in the dark for 17 h, followed by the addition of ion exchange resin (strongly basic, Dowex 1×50 carbonate form, 3 g). The resulting mixture was stirred for 0.5 h, filtered though a plug of celite (10 g, rinsing with DCM/MeOH, 1:1, 100 mL), and concentrated to give a dark brown oil. Purification via column chromatography (silica gel, 40 g, DCM/MeOH 85:15 as eluent) gave 40 mg (75%) of 2a as a tan solid. Alternatively, the triethylammonium salt may be removed without adding ion exchange resin by careful column chromatography.

Preparation of 2e: To a solution of 16 (100 mg, 0.24 mmol) in dry DMF (2 mL) at room temperature was added 28 (130 µL, 0.74 mmol), cuprous iodide (CuI, 9 mg, 0.05 mmol), tetrakis(triphenylphosphine)palladium(0) (57 mg, 0.05 mmol), and Et$_3$N (100 µL, 0.74 mmol). The reaction mixture was stirred in the dark for 17 h and concentrated to give a dark brown oil. Purification via column chromatography (silica gel, 40 g, DCM/MeOH 95:5, 90/10, 85/15 200 mL each, as eluent) gave 60 mg (53%) of 2e as a tan solid.

Preparation of rC-PA-NHTFA (3a): To a stirring solution of 15 (100 mg, 0.27 mmol) in DMF (4 mL) was added in the following order N-3-trifluoroacetamido-1-propyne 27 (PA-linker, 200 µL, 1.35 mmol), triethylamine, (TEA, 115 µL, 0.81 mmol), cuprous iodide (CuI, 15 mg, 0.08 mmol), and tetrakis(triphenylphosphine)palladium (35 mg, 0.027 mmol). The reaction mixture was stirred for 72 h, followed by the addition of Dowex-1 carbonate form (3 g). The quenched reaction mixture was filtered over a plug of celite (10 g), and rinsed with DCM/MeOH (1:1, 200 mL). The filtrate was concentrated and the crude product was purified by column chromatography [silica gel, 50 g, eluting with DCM/MeOH (9:1, 200 mL) followed by DCM/MeOH (8:2, 200 mL)] to give 60 mg of 3a (57%) as a brown solid.

Preparation of rC-EO-NHTFA (3e): To a stirring solution of 15 (100 mg, 0.26 mmol) in DMF (1 mL) was added in the following order 3-ethyloxy-[2'-N-trifluoroacetamido-]-1-propyne 28 (EO-linker, 140 µL, 0.76 mmol), TEA (110 µL, 0.76 mmol), CuI (10 mg, 0.05 mmol), and tetrakis(triphenylphosphine)palladium (30 mg, 0.027 mmol). The reaction mixture was stirred for 23 h, followed by quenching with Dowex-1 carbonate form (3 g). The quenched reaction mixture filtered over a plug of celite (10 g) and rinsed with DCM/MeOH (1:1, 100 mL). The filtrate was concentrated and the crude product was purified by column chromatography [silica gel, 50 g, eluting with DCM/MeOH (85:15, 200 mL), then DCM/MeOH (80:20, 100 mL)] to give a mixture of 3e/15 (8:1) as a brown solid mixture.

Preparation of rC-PA-NHTFA (3a) using 5-Bromocytidine (15b): To a stirring solution of 15b (250 mg, 0.78 mmol) in DMF (5 mL) was added in the following order N-3-trifluoroacetamido-1-propyne 27 (PA-linker, 320 µL, 2.33 mmol), triethylamine, (TEA, 320 µL, 2.33 mmol), cuprous iodide (CuI, 30 mg, 0.16 mmol), and tetrakis(triphenylphosphine)palladium (540 mg, 0.47 mmol). The reaction mixture was placed in a pre-heated oil bath at 80° C. and stirred for 4 h. The reaction mixture was concentrated, diluted with DCM/MeOH (80/20, 5 mL), and purified via column chromatography (silica gel, 50 g, 9/1 DCM/MeOH, 200 mL, then DCM/MeOH 80/20) to give 150 mg of 3a (50%) as a brown solid (90% HPLC purity).

Preparation of r-C-EO-NHTFA (3e) using 5-Bromocytidine (15b): To a stirring solution of 15b (100 mg, 0.31 mmol) in dry DMF (2 mL) was added 3-ethyloxy-[2'-N-trifluoroacetamido-]-1-propyne 28 (EO-linker, 170 µL, 0.93 mmol), CuI (15 mg, 0.079 mmol), tetrakis(triphenylphosphine)palladium (150 mg, 0.13 mmol)[2], and TEA (110 µL, 0.76 mmol) at room temperature. The reaction mixture was placed in a pre-heated oil bath at 80° C. and stirred for 1.5 h. The reaction mixture was cooled to room temperature followed by the addition of Dowex-1 carbonate form (3 g) and allowed to stir for an additional 0.5 h. The solution was filtered over a plug of celite (10 g) and rinsed with DCM/MeOH (1:1, 100 mL). The filtrate was concentrated and purified by column chromatography [silica gel, 50 g, eluting with DCM/MeOH (90:10, 200 mL), then DCM/MeOH (80:20, 100 mL)] to give 70 mg of 3e (52%).

Example 6

TRIPHOSPHATE SYNTHESIS General Procedure.
Reference: Ludwig, J. Acta Biochim. et Biophys. Acad. Sci. Hung., 16:131 (1981).

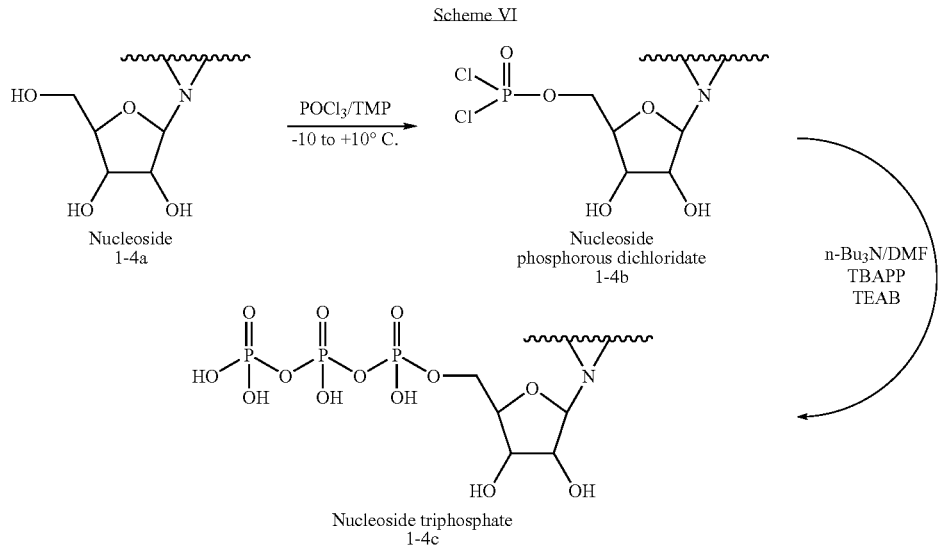

In Scheme VI, the nucleobase in compounds 1a, 1b, and 1c is adenosine; the nucleobase in compounds 2a, 2b, and 2c is guanosine; the nucleobase in compounds 3a, 3b, and 3c is cytosine; and the nucleobase in compounds 4a, 4b, and 4c is uridine.

To a stirring solution cooled to −10° C. of nucleoside (0.2 mmol) in dry trimethylphosphate (TMP; 0.5 mL) was added phosphorous oxychloride (POCl$_3$; 0.44 mmol, 2.2 eq.) via syringe. To monitor the progress of the reaction, 5 µL aliquots were taken from the reaction mixture, hydrolyzed in 0.2 mL of 0.1 M TEAB buffer, and 20 µL samples were analyzed by RP-HPLC using method A. The reaction was normally complete within 2-4 h, although, in some cases, longer reaction times were needed. In certain cases, additional POCl$_3$ was needed for the reaction to be completed (i.e., up to 6-8 equivalents). Additional POCl$_3$ did not effect the site of phosphate addition. After the reaction was complete, the reaction was quenched by the addition of a vigorously stirred solution of bis-tri-n-butylammonium pyrophosphate (TBAPP; 6 eq, 1.2 mmol), 0.5 M in dry dimethylformamide (DMF) (2.0 mL), and tri-n-butylamine (TBA; 10 eq, 2 mmol, 0.5 mL). The resulting reaction mixture was stirred for 1 min and then poured into a TEAB solution (1.0 M, 20 mL) at 0° C. The resulting solution was allowed to stand for a period of 3 h, concentrated, and purified via preparatory HPLC using method C. The resulting triphosphate was concentrated, taken up in 0.1 M TEAB (10-20 mL), and stored in the freezer at −20° C.

Preparation of rATP-PA-NHTFA (1c): To a stirring solution of anhydrous 1a (50 mg, 0.12 mmol) in dry TMP (1 mL) at −10° C. was added POCl$_3$ (99.999% Aldrich, 25 mL, 0.26 mmol). The reaction was monitored by HPLC (Method A, 5 µL aliquots in 100 µL 1 M TEAB). The retention time (RT) of 1a=11.7 min, the RT of 1b=9.1 min. An aliquot withdrawn from the reaction at 0.5 h showed a ratio of 47/41 1a/1b. An aliquot withdrawn at 1.5 h showed a ratio of 41/46 1a/1b. An aliquot withdrawn at 2.5 h showed a ratio of 33/64 1a/1b. An aliquot withdrawn at 7 h showed a ratio of 19/70 1a/1b. After 7 hours, the reaction mixture was tightly sealed, placed in the freezer at −20° C., and allowed to stand for 48 h. An aliquot of the reaction showed a ratio of 13/69 1a/1b. The reaction mixture was quenched by the addition of a vigorously stirred solution of TBAPP (330 mg, 0.72 mmol) in TBA (290 mL, 1.2 mmol) in DMF (1.0 mL) at 0° C. with stirring over a period of 1 min. This was followed by pouring the mixture into a solution of TEAB (1 M, 10 mL) at 0° C. The crude triphosphate 1c then was allowed to stand over a period of 1 h. The reaction mixture was concentrated to 4 mL and purified twice using preparatory HPLC (Method C,) to give 1c of suitable purity for the next step.

Preparation of rATP-EO-NHTFA (1g): To a stirring solution of 1e (90 mg, 0.20 mmol) prepared as in Example 6 in dry TMP (1.5 mL) at −10° C. was added POCl$_3$ (99.999% Aldrich, 40 µL, 0.43 mmol) from a freshly opened ampoule. The reaction was monitored by HPLC (Method A, 5 µL aliquots in 100 µL 1 M TEAB). The retention time (RT) of 1e=11.4 min. The RT of 1f (monophosphate)=8.6 min. An aliquot withdrawn from the reaction at 0.5 h showed a ratio of 1/1 1e/1f. An aliquot withdrawn at 1 h, 50 min showed a ratio of 1/3 1e/1f. After 4 h, a second 2.2 equivalents of POCl$_3$ (40 µL, 0.43 mmol) were added. The reaction mixture was tightly sealed, placed in the freezer at −20° C., and allowed to stand for 17 h. An aliquot of the reaction showed quantitative conversion to the monophosphate 1f. The reaction mixture was quenched by the addition of a vigorously stirred solution of TBAPP (900 mg, 2.0 mmol) in TBA (660 µL, 2.8 mmol) in DMF (2.0 mL) at 0° C. with stirring over a period of 1 min. This was followed by pouring the mixture into a solution of TEAB (0.1 M, 25 mL) at 0° C. and the crude triphosphate 1g was allowed to stand for 3 h. The reaction mixture was concentrated to 3 mL, filtered using a 0.2 micron in-line filter, and purified by preparatory HPLC (Method C) to give 1g of suitable purity for the next step.

Preparation of rGTP-PA-NHTFA (2c): To a stirring solution of 2a (38 mg, 0.09 mmol) prepared as in Example 6 in dry TMP (1.0 mL) at −10° C. was added POCl$_3$ (99.999% Aldrich, 18 µL, 0.19 mmol) from a freshly opened ampoule. The reaction was monitored by HPLC (Method A, 5 µL aliquots in 100 µL 1 M TEAB). The retention time (RT) of 2a=10.4 min. The RT of 2b (5'-O-monophosphate)=8.1 min. An aliquot withdrawn from the reaction at 0.33 h showed a ratio of 19/1 2a/2b. An aliquot withdrawn at 1 h, 50 min showed a ratio of 9/1 2a/2b. The reaction mixture was tightly sealed, placed in the freezer at −20° C., and allowed to stand for 17 h. HPLC analysis showed a ratio of 3/1 2a/2b. After 2 h, an additional 1.5 equivalents of POCl$_3$ (12 µL, 0.13 mmol) was added with stirring at 0° C. HPLC analysis of the reaction after a further 3 h, 40 min showed a ratio of 1/1 2a/2b. An additional 1.5 equivalents of POCl$_3$ (12 µL, 0.13 mmol; 5.2 equivalents total) was added while maintaining the reaction temperature between 4 and −10° C. The reaction mixture was tightly sealed, placed in the freezer at −20° C., and allowed to stand for 18 h. HPLC analysis of the reaction after this period showed a ratio of 0.8/1 2a/2b. Addition of a third 1.5 eq of POCl$_3$ (12 µL, 0.13 mmol) was made with stirring at 0° C. over a period of 2.25 h. The reaction mixture again was sealed and placed in the freezer at −20° C. for 48 h. HPLC showed a ratio of 78/12 2b/2a. The reaction mixture was quenched by the addition of a vigorously stirred solution of TBAPP (720 mg, 1.6 mmol) in TBA (630 µL, 2.7 mmol) in DMF (2.0 mL) at 0° C. with stirring over a period of 1 min. This was followed by pouring the mixture into a solution of TEAB (0.1 M, 25 mL) at 0° C. and the crude triphosphate 2c was allowed to stand for 3 h. The reaction mixture was concentrated to 3-4 mL, filtered using a 0.2 micron in-line filter, and purified using preparatory HPLC (Method C). This purification was repeated to give 2c of suitable purity for the next step. $^{31}$P NMR showed a 10/1 ratio of 2c/2b.

Preparation of rGTP-EO-NHTFA (2g): To a stirring solution of 2e (33 mg, 0.07 mmol) prepared as in Example 6 in dry TMP (1.0 mL) at −10° C. was added POCl$_3$ (99.999% Aldrich, 26 µL, 0.28 mmol, 4 eq.). Another 4 equivalents of POCl$_3$ (99.999% Aldrich, 26 µL, 0.28 mmol) were added after 1.5 h, while the reaction temperature was maintained between 4 and −10° C. The reaction mixture was tightly sealed, placed in the freezer at −20° C. and allowed to stand for 24 h. HPLC (Method A, 5 µL aliquots in 100 µL 1 M TEAB) showed that the starting material 2e (RT=10.2 min) was consumed with the appearance of the 5'-O-monophosphate 2f (RT=7.8 min). The reaction mixture was quenched by the addition of a vigorously stirred solution of TBAPP (280 mg, 0.62 mmol) in TBA (215 µL, 0.9 mmol) in DMF (1.0 mL) at 0° C. with stirring over a period of 1 min. This was followed by pouring the mixture into a solution of TEAB (0.1 M, 20 mL) at 0° C. and the crude triphosphate 2g was allowed to stand for 3 h. The reaction mixture was concentrated to 3-4 mL, filtered using a 0.2 micron in-line filter, and purified via preparatory HPLC (Method C) followed by flash ion exchange chromatography (DEAE Sephadex, 25A, 2 g) using a stepwise gradient of 0.1 M TEAB (100 mL), 0.25 M TEAB (100 mL), 0.3 M TEAB (50 mL), 0.35 M TEAB (50 mL), 0.38 M TEAB (50 mL), 0.42 M TEAB (50 mL), 0.45 M TEAB (50 mL), 0.5 M TEAB (50 mL), 0.6 M TEAB (50 mL), 0.7 M TEAB (50 mL), 0.8 M TEAB (50 mL), 1.0 M TEAB (50 mL). Fractions (0.42 M-1.0 M TEAB, analysis by $^{31}$P NMR) were pooled and concentrated to give 3 mL of a 5.4 mM solution of triphosphate 2g of suitable purity for the next step.

Preparation of rCTP-PA-NHTFA (3c): To a stirring solution of 3a (50 mg, 0.13 mmol) prepared as in Example 6 in dry TMP (1 mL) at −10° C. was added POCl$_3$ (99.999% Aldrich, 26 µL, 0.28 mmol). The reaction was monitored by HPLC (Method A, 5 µL aliquots in 100 µL 1 M TEAB). The retention time (RT) of 3a=9.6 min. The RT of 3b=7.6 min. At 0.5 h, the ratio of 3a/3b was 3/1. An aliquot withdrawn at 1.5 h showed a 3a/3b ratio of 45/40. An aliquot withdrawn at 5 h showed a 3a/3b ratio of 20/61. The reaction mixture was tightly sealed, placed in the freezer at −20° C., and allowed to stand for 48 h. An aliquot of the reaction mixture showed mostly 3b. The reaction mixture was quenched by the addition of a vigorously stirred solution of TBAPP (350 mg, 0.76 mmol) in TBA (300 µL, 1.3 mmol) in DMF (1.0 mL) at 0° C. with stirring over a period of 1 min. This was followed by pouring the mixture into a solution of TEAB (0.1 M, 25 mL) at 0° C. and the crude triphosphate 3c was allowed to stand for 3 h. The reaction mixture was concentrated to 4 mL and purified using preparatory HPLC (Method C) to give 3c of suitable purity for the next step.

Preparation of rCTP-EO-NHTFA (3g): To a stirring solution of 3e (70 mg, 0.16 mmol) prepared as in Example 6 in dry TMP (1.0 mL) at −10° C. was added POCl$_3$ (99.999% Aldrich, 33 µL, 0.35 mmol) from a freshly opened ampoule. The reaction was monitored by HPLC (Method A, 5 µL aliquots in 100 µL 1 M TEAB). The RT of 3e=9.4 min. The RT of 3f (monophosphate)=7.3 min. At 0.5 h, the ratio of 3f/3e was 3/1. The reaction mixture was tightly sealed and placed in the freezer at −20° C. and allowed to stand for 17 h. An aliquot of the reaction showed a 3f/3e ratio of 4/1. A second portion of POCl$_3$ (99.999% Aldrich, 33 µL, 0.32 mmol, 2.2 eq) was added at a temperature between 0° C. and −10° C. and the reaction mixture was stirred for 15 min. The reaction mixture then was quenched by the addition of a vigorously stirred solution of TBAPP (500 mg, 1.1 mmol) in TBA (400 µL, 1.7 mmol) in DMF (1.0 mL) at 0° C. with stirring over a period of 1 min. This was followed by pouring the mixture into a solution of TEAB (0.1 M, 25 mL) at 0° C. and the crude triphosphate 3g was allowed to stand for 2-3 h. The reaction mixture was concentrated to 3 mL, filtered using a 0.2 micron in-line filter, and purified using preparatory HPLC Method C) to give 3g of suitable purity for the next step.

Preparation of rUTP-PA-NHTFA (4c): To a stirring solution of 4a (prepared from 5-iodouracil as exemplified for 3a, 50 mg, 0.13 mmol) in dry TMP (0.5 mL) at −10° C. was added POCl$_3$ (99.999% Aldrich, 26 µL, 0.28 mmol). The reaction was monitored by HPLC (Method A, 5 µL aliquots in 100 µL 1 M TEAB). The RT of 4a RT=8.8 min. The RT of 4b=6.8 min. At 0.75 h, the ratio of 4a/4b was 9/1. An aliquot withdrawn at 5 h showed a 4a/4b ratio of 45/55. The reaction mixture was tightly sealed and placed in the freezer at 4° C. and allowed to stand for 18 h. An aliquot of the reaction mixture showed mostly 4b. The reaction mixture was quenched by the addition of a vigorously stirred solution of TBAPP (290 mg, 0.64 mmol) in TBA (210 µL, 0.89 mmol) in DMF (1.0 mL) at 0° C. with stirring over a period of 1 min. This was followed by pouring the mixture into a solution of TEAB (0.1 M, 40 mL) at 0° C. and the crude triphosphate 4c was allowed to stand for 3 h. The reaction mixture was concentrated to 4 mL and purified using preparatory HPLC (Waters, Delta Prep, Method C, Appendix II) to give 4c of suitable purity for the next step.

Preparation of rUTP-EO-NHTFA (4g): To a stirring solution of 4e (prepared from 5-iodouracil as exemplified for 3e, 50 mg, 0.11 mmol) in dry TMP (0.5 mL) at −5° C. was added POCl$_3$ (99.999% Aldrich, 33 µL, 0.35 mmol) from a freshly opened ampoule. The reaction mixture was tightly sealed, placed in the freezer at −20° C., and allowed to stand for 17 h. The reaction was monitored by HPLC (Method A, 5 µL aliquots in 100 µL 1 M TEAB). An aliquot of the reaction showed 14/1 4e/4f (RT of 4e=8.9 min, RT of 4f (monophosphate)=7.4 min). After stirring for 0.5 h, a second portion of POCl$_3$ (99.999% Aldrich, 33 µL, 0.32 mmol, 2.2 eq)) was added at a temperature between 0° C. and −10° C. and the reaction mixture was allowed to stir for 10 min. An aliquot of the reaction mixture showed a 4e/4f ratio of 5/1. After stirring for an additional 5 h, a third portion of POCl$_3$ (99.999% Aldrich, 33 µL, 0.32 mmol, 2.2 eq)) was added at a temperature between 0° C. and −10° C. and the reaction mixture was stirred for 0.5 h. An aliquot of the reaction mixture showed a 4e/4f ratio of 1/1. The reaction mixture was tightly sealed, placed in the freezer at −20° C., and allowed to stand for 17 h. The reaction mixture was removed from the freezer and stirred at 0° C. for 1 h, 15 min followed by the addition of a vigorously stirred solution of TBAPP (720 mg, 1.6 mmol) in TBA (540 µL, 2.3 mmol) in DMF (2.0 mL) at 0° C. After stirring for 2 min, the reaction mixture was poured into TEAB (0.1 M, 25 mL) at 0° C. and the crude triphosphate 4g was allowed to stand for 2-3 h. The reaction mixture was concentrated to 3 mL, filtered using a 0.2 micron in-line filter, and purified using preparatory HPLC (Method C) to give 4g of suitable purity for the next step.

Example 7

TRIFLUOROACETAMIDE DEPROTECTION AND NUCLEOTIDE FORMULATION: General Procedure.

The nucleoside triphosphate in 0.1 M TEAB buffer was concentrated essentially to dryness via rotary evaporation. The resulting sample was diluted with ammonium hydroxide (5-10 mL), the solution was allowed to stir at room temperature for the appropriate period of time (0.5 to 3 h) and then concentrated. The remaining NH$_4$OH was removed via co-evaporation with 0.1 M TEAB (2×10-20 mL). The deprotected nucleotide was diluted with 0.1 M TEAB (3-5 mL) and the concentration and yield were determined according to Beer's Law (Equation 1) using the following extinction coefficients for the deoxyribose nucleosides: dATP=15,200, dCTP=9,300, dGTP=13,700, dUTP=9,600.

$$C_{mM} = [(A \cdot \text{Vol}_{tot}/\text{Vol}_{sample})/(\epsilon_{nucleoside\ cm^{-1}\ M^{-1}} \cdot b)] \times 1000 \quad \text{Equation 1}$$

Where $C_{mM}$ is the concentration (millimolar, mM), A is the observed absorbance, $\text{Vol}_{tot}$ and $\text{Vol}_{sample}$, are the total and sample volumes, respectively, b is the path length, and $\epsilon$ is the molar extinction coefficient.

Preparation of rATP-PA-NH$_2$ (1d): A solution of 1c in 0.1 M TEAB (~10 mL) was concentrated followed by dilution with concentrated NH$_4$OH (5 mL). The reaction mixture was stirred for 40 min and concentrated using a rotary evaporator. The remaining NH$_4$OH was removed by diluting the residue with 0.1 M TEAB (5 mL) and re-concentrating. This was repeated 2 times. Formulation in 0.1 M TEAB gave a 12.09 mM solution of 1d ($\lambda_{max}$ 280 nm, ~6 mL, 60 µmol, 50%, from 1a).

Preparation of rATP-EO-NH$_2$ (1h): A solution of 1g in 0.1 M TEAB (~10 mL) was concentrated followed by dilution with concentrated NH$_4$OH (6 mL). The reaction mixture was stirred for 3 h and concentrated using a rotary evaporator. The remaining NH$_4$OH was removed by diluting the residue with 0.1 M TEAB (5 mL) and re-concentrating. This was repeated 2 times. Formulation in 0.1 M TEAB gave a 17.7 mM solution of 1h ($\lambda_{max}$ 280 nm, ~7 mL, 124 µmol, 62% from 1e).

Preparation of rGTP-PA-NH$_2$ (2d): A solution of 2c in 0.1 M TEAB (~10 mL) was concentrated followed by dilution with concentrated NH$_4$OH (7 mL). The reaction mixture was stirred for 30 min and concentrated using a rotary evaporator. The remaining NH$_4$OH was removed by diluting the residue with 0.1 M TEAB (5 mL) and re-concentrating. This was repeated 2 times. Formulation in 0.1 M TEAB gave ~3 mL of a 7.96 mM solution of 2d ($\lambda_{max}$ 234 nm, 274 nm, 292 nm); Low Resolution MS, M-1, 574), 24 µmol, 27%, from 2a).

Preparation of rGTP-EO-NH$_2$ (2h): A solution of 2g in 0.1 M TEAB (~10 mL) was concentrated followed by dilution with concentrated NH$_4$OH (7 mL). The reaction mixture was stirred for 30 min and concentrated using a rotary evaporator. The remaining NH$_4$OH was removed by diluting the residue with 0.1 M TEAB (5 mL) and re-concentrating. This was repeated 2 times. Formulation in 0.1 M TEAB gave ~5 mL of a 5.37 mM solution of 2h ($\lambda_{max}$ 238 nm, 274 nm, 292 nm); Low Resolution MS, M-1, 618, RT$_{method\ A}$=5.2 min), 27 µmol, 26%, from 2e).

Preparation of rCTP-PA-NH$_2$ (3d): A solution of 3c in 0.1 M TEAB (~10 mL) was concentrated followed by dilution with concentrated NH$_4$OH (5 mL). The reaction mixture was stirred for 2.5 h and concentrated by rotary evaporation. The remaining NH$_4$OH was removed by diluting the residue with 0.1 M TEAB (5 mL) and re-concentrating. This was repeated 2 times. Formulation in 0.1 M TEAB gave 3 mL of a 9.7 mM solution of 3d ($\lambda_{max}$ 238 nm, 296 nm; 29 µmol, 23%, from 3a).

Preparation of rCTP-EO-NH$_2$ (3h): A solution of 3g in 0.1 M TEAB (~10 mL) was concentrated followed by dilution with concentrated NH$_4$OH (5 mL). The reaction mixture was stirred for 3 h and concentrated, by rotary evaporation. The remaining NH$_4$OH was removed by diluting the residue with 0.1 M TEAB (5 mL) and re-concentrating. This was repeated 2 times. Formulation in 0.1 M TEAB gave 4.5 mL of a 13.5 mM solution of 3h ($\lambda_{max}$ 296 nm, 61 µmol, 38%, from 3e).

Preparation of rUTP-PA-NH$_2$ (4d): A solution of 4c in 0.1 M TEAB (~10 mL) was concentrated followed by dilution with concentrated NH$_4$OH (5 mL). The reaction mixture was stirred for 4 h and concentrated by rotary evaporation. The remaining NH$_4$OH was removed by diluting the residue with 0.1 M TEAB (5 mL) and re-concentrating. This was repeated 2 times. Formulation in 0.1 M TEAB gave 1 mL of a 13.5 mM solution of 4d ($\lambda_{max}$ 234 nm, 288 nm, 14 µmol, 11%, from 4a).

Preparation of rUTP-EO-NH$_2$ (4h): A solution of 4g in 0.1 M TEAB (~10 mL) was concentrated followed by dilution with concentrated NH$_4$OH (5 mL). The reaction mixture was stirred for 3 h and concentrated by rotary evaporation. The remaining NH$_4$OH was removed by diluting the residue with 0.1 M TEAB (5 mL) and re-concentrating. This was repeated 2 times. Formulation in 0.1 M TEAB gave 3 mL of a 6.5 mM solution of 4h ($\lambda_{max}$ 232 nm, 292 nm, 20 µmol, 17%, from 4e).

Example 8

DYE-NUCLEOSIDE COUPLING: General Procedure.

Approximately 0.3 µmol of ribonucleotide triphosphate in 0.1 M TEAB was concentrated to dryness with a centrifuge-vacuum apparatus (e.g., a Speed-Vac). The resulting solid was dissolved in sodium bicarbonate (250 mM, 50 µL) adjusted to pH 9 with 1.0 M NaOH followed by the addition of the dye-NHS ester (0.8 µmol, 5 µL, conc.=5 mg/60 µL DMSO, 2.7 eq), mixed, and allowed to stand for 17 h. The reaction mixture was briefly centrifuged to remove particulates and the reaction mixture was purified via ion exchange HPLC followed by RP-C8 HPLC according to the procedures described in Example 1. When TEAA buffer was used in the RP-C8 purification step, TEAB was added to prevent acid build-up during concentration. After RP-C8 purification, the dye-labeled ribonucleotide triphosphate was formulated in 3-[cyclohexylamino]-2-hydroxy-1-propanesulfonic acid (CAPSO, 50 mM, 50-100 µL). A 5 µL portion was diluted with 0.1 M TEAB (500 µL) and an UV spectrum was obtained. The concentration (mM) was calculated from Equation 2.

$$C_{mM} = [(A \cdot \text{Vol}_{tot}/\text{Vol}_{sample})/(\epsilon_{dye\ cm}^{-1}{}_M^{-1} \cdot b)] \times 1000 \quad \text{Equation 2}$$

where $\epsilon_{dye\ cm}^{-1}$ is the molar extinction of the dye. Solutions of dye-labeled ribonucleotide analogs were prepared at the following concentrations:

rATP-PA-5-R6G (1i): 505 µM in 95 µL of 50 mM CAPSO.
rATP-PA-d-R6G-2 (1j): 104 µM in 25 µL of 50 mM CAPSO.
rATP-EO-5-R6G (1k): 758 µM in 95 µL of 50 mM CAPSO.
rATP-EO-d-R6G-2 (1l): 34 µM in 95 µL of 50 mM CAPSO.
rGTP-PA-5-R110 (1j): 63 µM in 25 µL of 50 mM CAPSO.
rGTP-PA-d-R110-2 (2j): 664 µM in 45 µL of 50 mM CAPSO.
rGTP-EO-5-R110 (2k): 123 µM in 25 µL of 50 mM CAPSO.
rGTP-EO-d-R110-2 (2l): 173 µM in 55 µL of 50 mM CAPSO.
rCTP-PA-6-ROX (3i): 162 µM in 115 µL of 50 mM CAPSO.
rCTP-PA-d-ROX-2 (3j): 121 µM in 55 µL of 50 mM CAPSO.
rCTP-EO-6-ROX (3k): 71 µM in 95 µL of 50 mM CAPSO.
rCTP-EO-d-ROX-2 (3l): 172 µM in 55 µL of 50 mM CAPSO.
rUTP-PA-6-TAMRA (4i): 684 µM in 95 µL of 50 mM CAPSO.
rUTP-PA-d-TAMRA-2 (4j): 818 µM in 95 µL of 50 mM CAPSO.
rUTP-EO-6-TAMRA (4k): 404 µM in 95 µL of 50 mM CAPSO.
rUTP-EO-d-TAMRA-2 (4l): 343 µM in 95 µL of 50 mM CAPSO,
rUTP-EO-d-ROX-2 (4m): 174 µM in 55 µL of 50 mM CAPSO.

In the list above, EO represents an propargyl-ethyl-oxide-amino linker and PA represents a propargyl amine linker. The dyes are abbreviated as follows: R6G (rhodamine 6G), R6G-2 (rhodamine 6G-2), R110 (rhodamine 110), ROX (rhodamine X), ROX-2 (rhodamine X-2), and TAMRA (tetramethylrhodamine).

Example 9

ENERGY TRANSFER DYE-NUCLEOSIDE COUPLING: General Procedure. See U.S. Pat. No. 5,945,526 to Lee et al.

Approximately 0.6 µmol of ribonucleotide triphosphate in 0.1 M TEAB was concentrated to dryness with a centrifuge-vacuum apparatus (e.g., a Speed-Vac). The resulting solid was dissolved in sodium bicarbonate (250 mM, 50 mL) adjusted to pH 9 with 1.0 M NaOH followed by the addition of the 5-carboxyfluorescein-NHS ester (FAM-NHS ester) for rGTP-EO-Energy transfer dye or 6-FAM-NHS ester for all other energy transfer dye pairs (1.6 µmol, 10 µL, conc.=5 mg/60 µL DMSO, 2.7 eq), mixed, and allowed to stand for 2-17 h. The reaction mixture was briefly centrifuged to remove particulates and the reaction mixture was purified via ion exchange followed by RP-C8 HPLC as described in Example 1. The resulting FAM-labeled ribonucleotide triphosphate was concentrated and the Fmoc moiety was removed by dissolving the product in concentrated $NH_4OH$ (300 µL) and heating at a temperature between 55-60° C. for 0.5 h.

The deprotected FAM-labeled nucleotide was purified via RP-C8 HPLC, concentrated to dryness, and coupled to the appropriate dichlororhodamine (e.g. rUTP-EO-6-FAM-dTAMRA 4o, rCTP-EO-6-FAM-dROX 3p, rATP-PA-6-FAM-dR6G 1j, and rGTP-EO-5-FAM-dR110 2n). Except for A-PA-6-FAM-dR6G, the energy transfer dye coupling was performed in sodium bicarbonate buffer (0.25 M, pH=9 (adjusted with NaOH)). For the synthesis of A-PA-6-FAM-dR6G 1j, bis(trifluoroacetamido)-dR6G-NHS ester was used. This protected dye is not soluble in aqueous buffer; hence the reactions were performed in freshly-distilled formamide. A 5 µL portion was diluted with 0.1 M TEAB (500 µL) and a UV spectrum was obtained. The concentration (mM) is calculated from Equation 2 above, with the following results:

rATP-PA-6-FAM-d-R6G (1m): 125 µM in 100 mM TEAB.
rGTP-EO-5-FAM-d-R110 (2m): 106 µM in 100 mM TEAB.
rCTP-EO-6-FAM-d-ROX (3m): 71 µM in 100 mM TEAB.
rCTP-EO-6-FAM-d-TAMRA (3o): 138 µM in 100 mM TEAB.
rUTP-EO-6-FAM-d-TAMRA (4m): 144 µM in 100 mM TEAB.

Example 10

This example demonstrates the use of the dye-labeled compounds of the invention in the direct PCR sequencing of DNA. The twenty microliter reaction mixture comprised 25 mM Tris-Cl, pH 8.8 at 20° C., 1 mM β-mercaptoethanol, 50 mM KCl, 1.25 mM $MgCl_2$, 100 µM dATP, 100 µM dCTP, 100 µM dGTP, 100 µM dUTP, biotinylated forward primer (200 nM; −21 M13 forward primer), reverse primer (200 nM, M13 reverse primer), 50 nM rUTP-PA-6-TAMRA (4i), 50 nM rCTP-PA-6-Rox (3i), 50 nM rGTP-PA-5-R110 (2i), 25 nM rATP-PA-6-R6G (1i), 0.75 units of Tma polymerase 25R, 3 units of Tma polymerase 30R, 2.5 units of Taq polymerase, and 6 ng of template DNA (pGEM 3Zf(+)).

Tma polymerase 25R and Tma polymerase 30R are described in U.S. Pat. No. 5,939,292, which is hereby incorporated by reference herein. The enzymes are, respectively, proofreading and non-proofreading versions of novel thermostable DNA polymerases, which comprise a mutation that increases the efficiency of ribonucleotide incorporation. Specifically, each enzyme has a mutation at Tma codon 678 that changes E678 to glycine.

The reaction mixture was placed in a thermal cycler, heated to 95° C. for 45 seconds, and then subjected to 45 cycles of 95° C. for 15 seconds, 55° C. for 30 seconds, and 65° C. for 3 minutes. The final incubation at 65° C. was continued for an additional 10 minutes. One microliter of the reaction mixture was analyzed on a 2% agarose gel to confirm that the amplicon was a unique band.

The remaining 19 µl reaction was mixed with 2 µl 250 mM EDTA and 10 µl 1 N NaOH and heated to 98° C. for 10 minutes in order to hydrolyze the primer extension products at sites of dye-labeled rNTP incorporation. The solution was cooled and neutralized by the addition of 10 µl 1 N HCl. Fragments containing the forward primer were captured on 5 µl of avidin-coupled magnetized beads (Dynabeads®) and washed with 70% ethanol. The captured fragments were eluted from the beads by heating to 98° C. for 2 minutes in 3 µl loading buffer (50% formamide (v/v) containing bromophenol blue) and analyzed on an Applied Biosystems 377 DNA Sequencer. The sequence determined, which extended through the complete multicloning site between the forward and reverse primers base pairs from the forward primer, matched the known sequence of pGEM 3Zf(+).

Alternative methods of cleaving the dye-labeled ribonucleotide-containing amplicons will be appatent to those skilled in the art. For example, a mix of various RNAses may be employed. In this case, an appropriate amount of a commercially-available blend of RNAses, e.g., RiboShredder® (Epicentre Technologies, Madison, Wis.), is added to the 20 µl amplification mix and reacted according to the manufacturers protocols; or a homemade blend of RNAses (RNAses H, A, T1 etc) can be made, added to the 20 µl of amplification product and reacted at 37° C. for 1-2 hours. Alternatively, amplicons may be cleaved simply by heating, although, the time of heating preferably is increased from the 10 minutes used in the alkali/heating protocol to at least 45 minutes at 98° C.

Example 11

The dye-labeled ribonucleotides of the invention also may be used to detect SNPs directly in genomic DNA by performing PCR using two oligonucleotide primers that anneal with sequences located sufficiently close to each other to provide a small amplicon. To exemplify one such method, which is schematically illustrated in FIG. 1, a twenty microliter reaction mixture comprising 25 mM Tris-Cl, pH 8.8 at 20° C., 1 mM β-mercaptoethanol, 50 mM KCl, 1.25 mM MgCl$_2$, 100 µM dATP, 100 µM dCTP, 100 µM dGTP, 100 µM dUTP, 1.25 µM primer A (23 nucleotides in length), 1.25 µM primer B (21 nucleotides in length), 50 nM rUTP-PA-TAMRA, 50 nM rCTP-PA-Rox, 50 nM rGTP-PA-R110, 25 nM rATP-PA-5R6G, 0.75 units of Tma polymerase 25R, 3 units of Tma polymerase 30R, 2.5 units of Taq polymerase, and 50 ng of total genomic DNA was made. Primer B was designed so that the first base added to the primer by the polymerases is the SNP of interest. Because primer A was longer than primer B, the band corresponding to the SNP position was not covered by a band from the opposite strand. There was therefore no need to separate the two microsequence ladders prior to electrophoresis.

The reaction mixture was placed in a thermal cycler, heated to 94° C. for 10 minutes, and then subjected to 45 cycles of 94° C. for 15 seconds, 55° C. for 5 seconds, and 65° C. for 30 seconds. One microliter of the reaction mixture was analyzed on a 2% agarose gel to confirm that the amplicon was a unique band.

The remaining 19 µl reaction was mixed with 2 µl 250 mM EDTA and 10 µl 1 N NaOH and heated to 98° C. for 10 minutes in order to hydrolyze the primer extension products at sites of dye-labeled rNTP incorporation. The solution was cooled and neutralized by the addition of 10 µl 1 N HCl. Loading buffer (20 µl) was added to each sample and 2.5 µl of each sample were analyzed on an 16% denaturing polyacrylamide gel on an Applied Biosystems 377 DNA Sequencer.

The results of the electrophoretic separation are diagramed in FIG. 1. Because primer B was shorter than primer A, the first band that was seen on the gel corresponded to the SNP on the minus strand of the genomic DNA template, in this case an adenine.

Example 12

This example demonstrates the use of the dye-labeled compounds of the invention to detect SNPs on both strands of a DNA template in a single reaction, as illustrated in FIG. 2. The reaction conditions were the same as those for Example 11, except for the primers, which were 24 (primer C) and 26 (primer D) nucleotides in length, and the amount of genomic DNA template, 75 ng. Both primers were designed so that the first base added to each by the polymerases is the SNP of interest.

The results of the electrophoretic separation of fragments containing the primers are diagramed in FIG. 2. Because primer C was shorter than primer A, the first band that was seen on the gel corresponded to the SNP on the minus strand of the genomic DNA template, in this case an adenine. The first band corresponding to the plus strand was a guanine, indicating that the template was heterozygous for this SNP.

Example 13

The DNA sequence of each strand surrounding a SNP may be unambiguously determined using the compounds of the invention. The reaction conditions again are the same as those in Example 11, except that primer E is 18 nucleotides in length and primer F comprises 22 nucleotides that are complementary to the target DNA and 30 nucleotides that are not complementary to the target DNA. Nucleotide 23 of primer F is a modified nucleotide, for example, an inverted base with a 5'-5' phosphodiester bond, that prevents 5'-extension of primer E beyond this point.

The resulting fragments after gel electrophoresis are illustrated in FIG. 3. Extension products of primer E range from 19 to 45 nucleotides in length, with the SNP present as the 21 nucleotide fragment. The extension products from primer F, which range in size from 53 to 76 nucleotides, are readily separated from the primer E-derived fragments. Again, the fragment identifying the SNP is the third fragment.

The DNA sequence of each strand surrounding a SNP may also be unambiguously determined using the compounds of the invention, if the primers used are separated after hydrolysis, for example by hybridization to complementary sequences. As diagramed in FIG. 4, primer G comprises hybridization based pull-out (HBP) sequence 1 and primer H comprises HBP sequence 2. After hydrolysis with base, the fragments comprising primers G and H can be separated from other fragments and from each other by hybridization to affinity matrices on which complementary oligonucleotides are immobilized by techniques known to those skilled in the art, for example, those disclosed in U.S. Pat. No. 6,124,092. After the fragments are eluted from the affinity matrices, the sequence of each strand is determined by gel electrophoresis.

Example 14

The dye-labeled compounds of the invention also are useful in an improved method for determining the methylation state of DNA, especially of promoter regions in genomic DNA. In this method, a bisulphite salt, preferable sodium bisulfite, is used to convert cytosine residues to uracil residues in the target DNA, under conditions whereby 5-methylcytosine remains non-reactive. Clark et al., Nucl. Acids Res. 22: 2990-97 (1994). The bisulfite-treated DNA is then amplified by PCR with primers specific for the region of interest in the presence of a dye-labeled rCTP analog according to the invention. One microliter of the reaction mixture is analyzed on a 2% agarose gel to confirm that the amplicon is a unique band.

The remaining 19 µl reaction is mixed with 2 µl 250 mM EDTA and 10 µl 1 N NaOH and heated to 98° C. for 10 minutes in order to hydrolyze the primer extension products at sites of dye-labeled rCTP incorporation. The solution is cooled and neutralized by the addition of 10 µl 1 N HCl. Loading buffer (20 µl) is added to each sample and 2.5 µl of each sample is analyzed on an 5% denaturing polyacrylamide gel on an Applied Biosystems 377 DNA Sequencer. All the cytosine residues remaining in the sequence correspond to methylated cytosines in the template DNA.

Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed is:

1. A compound having a structure of Formula I:

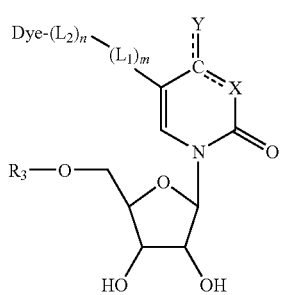

Formula I wherein X is N, NH, or C;
Y is O or $NH_2$;
$R_3$ is triphosphate, α-thiotriphosphate, or a salt thereof;
$L_1$ is a linker;
$L_2$ is a benzylamine linker;
n=0-4, m=0-4 and m+n is at least 1; and;
the dye is any reporter group.

2. The compound according to claim 1, wherein X is N and Y is $NH_2$.

3. The compound according to claim 1, wherein X is C and Y is O.

4. The compound according to claim 1 wherein $L_1$ is a propargyl-ethyloxide-amino linker, a propargylamino linker, a propargyl-propyl-oxide-amino linker, a benzylamine linker, a rigid linker, or a multimer thereof.

5. The compound according to claim 1, wherein m=1.

6. The compound according to claim 5, wherein $L_1$ is a propargyl-ethyloxide-amino linker or a propargylamino linker.

7. A compound having a structure of the Formula III:

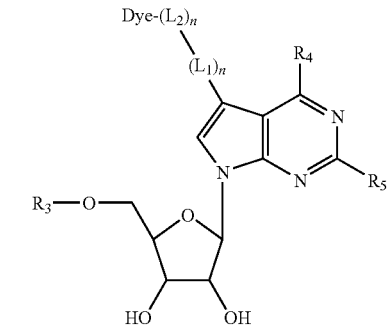

Formula III wherein $L_1$ is a linker;
$L_2$ is a benzylamine linker;
n=0-4, m=0-4, and m+n is at least 1;
R4 is $NH_2$, OH, or O, and $R_5$ is $NH_2$, OH, or H;
R3 is triphosphate, α-thiotriphosphate, or a salt thereof; and
the dye is any reporter group.

8. The compound according to claim 7, wherein $L_1$ is a propargyl-ethyloxide-amino linker, a propargylamino linker, a propargyl-propyl-oxide-amino linker, a benzylamine linker, a rigid linker, or a multimer thereof.

9. The compound according to claim 7, wherein n=1.

10. The compound according to claim 9, wherein $L_1$ is a propargyl-ethyloxide-amino linker or a propargylamino linker.

11. The compound according to claim 9, wherein $R_4$ is $NH_2$ and $R_5$ is H.

12. The compound according to claim 9, wherein $R_4$ is O and $R_5$ is $NH_2$.

* * * * *